(12) United States Patent
Steinberg et al.

(10) Patent No.: US 8,423,122 B2
(45) Date of Patent: Apr. 16, 2013

(54) LOCALIZATION OF CAPSULE WITH A SYNTHETIC SOURCE OF QUADRUPOLES AND DIPOLES

(75) Inventors: Ben Zion Steinberg, Kfar Saba (IL); Ido Bettesh, Zichron Ya'akov (IL)

(73) Assignee: Given Imaging Ltd., Yogneam (IL)

( * ) Notice: Subject to any disclaimer, the term of this patent is extended or adjusted under 35 U.S.C. 154(b) by 160 days.

(21) Appl. No.: 13/003,078

(22) PCT Filed: Jul. 6, 2009

(86) PCT No.: PCT/IL2009/000676
§ 371 (c)(1),
(2), (4) Date: Feb. 3, 2011

(87) PCT Pub. No.: WO2010/004555
PCT Pub. Date: Jan. 14, 2010

(65) Prior Publication Data
US 2011/0125007 A1 May 26, 2011

Related U.S. Application Data

(60) Provisional application No. 61/079,530, filed on Jul. 10, 2008.

(51) Int. Cl.
*A61B 5/05* (2006.01)
*G01S 5/04* (2006.01)

(52) U.S. Cl.
USPC .......................................... 600/424; 324/448

(58) Field of Classification Search .................. 600/114, 600/101, 130, 424, 476, 302, 30; 607/61, 607/29; 324/207.13, 207.15, 207.17, 207.26; 702/150–153
See application file for complete search history.

(56) References Cited

U.S. PATENT DOCUMENTS

| | | | |
|---|---|---|---|
| 3,868,565 A * | 2/1975 | Kuipers | 324/207.26 |
| 4,737,794 A * | 4/1988 | Jones | 342/448 |
| 4,742,536 A * | 5/1988 | Dewenter et al. | 379/93.09 |
| 5,307,072 A * | 4/1994 | Jones, Jr. | 342/147 |
| 5,604,531 A | 2/1997 | Iddan et al. | |
| 6,330,467 B1 | 12/2001 | Creighton, IV et al. | |
| 6,939,292 B2 * | 9/2005 | Mizuno | 600/118 |
| 7,009,634 B2 | 3/2006 | Iddan et al. | |
| 7,076,284 B2 * | 7/2006 | Segawa et al. | 600/424 |

(Continued)

FOREIGN PATENT DOCUMENTS
WO WO 2007/074445 7/2007

OTHER PUBLICATIONS

International Search Report of Application No. PCT/IL2009/000676 mailed on Dec. 4, 2009.

*Primary Examiner* — Long V. Le
*Assistant Examiner* — Lawrence Laryea
(74) *Attorney, Agent, or Firm* — Pearl Cohen Zedek Latzer, LLP

(57) ABSTRACT

This invention relates to methods and apparatus for localizing an in vivo imaging device by means of a single magnetic source coil assembly and a single magnetic detector coil assembly. This invention also relates to methods and apparatus to enable the use of a single magnetic source coil assembly to also transmit and receive information, images, and controls signals, as well as for the coil assembly to be used in DC-DC voltage conversion. A user interface with a display provides the user with the option of viewing selected images captured by the in vivo imaging device.

20 Claims, 17 Drawing Sheets

U.S. PATENT DOCUMENTS

| | | |
|---|---|---|
| 7,174,202 B2 * | 2/2007 | Bladen et al. .................. 600/424 |
| 7,657,300 B2 * | 2/2010 | Hunter et al. .................. 600/424 |
| 7,763,014 B2 * | 7/2010 | Houzego et al. ........... 604/890.1 |
| 2004/0199061 A1 | 10/2004 | Glukhovsky |
| 2005/0029437 A1 * | 2/2005 | Hasegawa et al. ............ 250/226 |
| 2007/0129602 A1 * | 6/2007 | Bettesh et al. ................ 600/118 |
| 2007/0181806 A1 | 8/2007 | Nakano et al. |
| 2008/0167523 A1 * | 7/2008 | Uchiyama et al. ............ 600/114 |

* cited by examiner

LOCALIZATION OF CAPSULE WITH A SYNTHETIC SOURCE OF QUADRUPOLES AND DIPOLES

CROSS-REFERENCE TO RELATED APPLICATIONS

This application is a National Phase Application of PCT International Application No. PCT/IL2009/000676, International Filing Date Jul. 6, 2009, entitled "Localization of Capsule with a Synthetic Source of Quadrupoles and Dipoles, published as International Publication Number WO 2010/004555, claiming priority of U.S. Patent Application 61/079,530, filed Jul. 10, 2008, which is incorporated herein by reference in its entirety.

FIELD OF INVENTION

The present invention relates to an in vivo device and method such as for imaging an in vivo lumen. More specifically, the present invention relates to a method and apparatus for an in vivo system for localizing an autonomous in vivo imaging device.

BACKGROUND OF THE INVENTION

Known devices may be helpful in providing in vivo sensing, such as imaging or pH sensing. Autonomous in vivo sensing devices, such as swallowable or ingestible capsules or other devices may move through a body lumen, sensing as they move along. An autonomous in vivo sensing device such as an imaging device may include, for example, an imager for obtaining images from inside a body cavity or lumen, such as the gastrointestinal (GI) tract while the in vivo imaging device passes through the GI lumen. The imager may, for example, be associated with an optical system, and optionally a transmitter and an antenna. Some of these devices use a wireless connection to transmit image data. Other devices, systems, and methods for in vivo sensing of passages or cavities within a body, and for sensing and gathering information (e.g., image information, pH information, temperature information, electrical impedance information, pressure information, etc.), are known in the art.

Since it is important not only to obtain images of the in vivo lumen, such as those of the GI tract, but also to know where these images were taken to be able to provide effective treatment, an accurate localization of the imaging device becomes an important task. A precise presentation of the localization of the imaging device, such as a swallowable capsule, would enable the operator of the apparatus to accurately determine where the in vivo the capsule was located when the image was captured.

Localization of an item in a three dimensional (3-D) space has been addressed by various methods and solutions. Typically, the larger the entity that needs to be localized, the closer the item to the localizing system, and the stronger the source of energy used for the localization, the easier the solution for localization. Localization of an entity in a 3-D space may, typically, return a set of three coordinates, for example X, Y, and Z parameters in a Cartesian system, and a set of three orientation parameters, indicating the orientation of the item with respect to a reference frame.

Various methods and systems for localization based on an electro-magnetic field are known. Magnetic localization methods are based on the use of a magnetic source that can generate a set of prescribed magnetic field patterns in a given domain in space, and a magnetic sensor designed to "read" the magnetic field. Traditionally, the magnetic source consists of three orthogonal magnetic dipoles (current loops, or source coils) that can be excited independently by time-varying currents of frequency $\omega$. The sensor consists of three orthogonal coils. The voltage excited across the terminal of a single sensor coil is proportional to $\omega H \cdot \hat{n}$, where H is the magnetic field, and $\hat{n}$ is a unit vector normal to the coil plane. Therefore, the three orthogonal sensor coils can be used to determine the local magnetic field, i.e. its strength and its direction relative to the sensor coordinate system (for example, the coordinate system defined by the three orthogonal sensor coils). The local magnetic fields for three linearly independent excitations (the source orthogonal dipoles) provide sufficient information to determine the sensor location. This is the principle of operation in traditional magnetic localization systems. However, in many applications the physical space and/or electronic resources that can be allocated for a source and/or a sensor are extremely limited. In such cases, a magnetic localization system utilizing a single-coil source and/or sensor may be of importance. One option is to use more than one set of dipole sources and/or sensors; say N sources and/or N sensors, each with its own distinct location $r_n$, n=1, . . . N−1 and orientation $\hat{v}_n$, n=1, . . . N−1 relative to the pre-defined "main" source and/or sensor, conveniently situated at $r_0$=0. If the relative locations and orientations of these N distinct sensors are known, then an algorithm for determining the location of the source coil can be derived, as described by H. C. Gilbert in "Dipole moment detector and localizer," U.S. Pat. No. 5,731,996. The main disadvantage of this approach is the need to have a precise knowledge of $r_n$ and $\hat{v}_n$. For example, in some medical applications it is desirable to locate the sources on the patient's body. In such a situation it may be difficult to measure their relative locations and orientations, and furthermore, these may vary in time due to patient's movements. A solution for accurate localization, which requires a small space and overcomes the drawbacks illustrated above, is thus required.

SUMMARY OF THE INVENTION

According to one embodiment of the present invention, a method and apparatus are disclosed for determination by a single coil sensor of the location of a single electromagnetic source comprising a set of three orthogonal dipoles and three orthogonal quadrupoles, said quadrupoles being synthesized from said dipoles.

In some embodiments, the system may include an electromagnetic source for localization, enabling the determination of substantially the precise location of an in vivo sensing device. In some embodiments, electromagnetic radiator source coils may serve as an external reference frame for enabling the localization of a device containing an electromagnetic detector coil. According to an embodiment of the invention, electromagnetic positioning source coils may be connected to an electromagnetic positioning locator, which may be included as part of a workstation. In some embodiments, a D/A converter may be used to supply proper current to an electromagnetic source for localization purposes.

In some embodiments, a single coil assembly may be used for one or more of three separate, distinct, and independent purposes: as a electromagnetic sensor used for localization of an in vivo imaging capsule; as a part of a DC-DC voltage step-up converter, which may be used, for example, for providing the capsule with power; and as part of an antenna transmit/receive system used for transmitting, for example, images from the capsule, receiving, for example, control instructions by the capsule, etc. According to some embodiments of the invention, time division multiplexing scheme may be utilized for using the coil assembly to achieve its multiple purposes.

In some embodiments, the system may include an in vivo imaging device having an optical sensor, one or more illumination sources, a power source, and a transceiver (a.k.a. transponder or transceiver). In some embodiments, an optical system may be implemented to enable enhanced imaging. In some embodiments, the device may include an in vivo image sensor, which may capture and transmit images of, for example, the GI tract while the device passes through the GI lumen.

In some embodiments, the in vivo device may be implemented using a swallowable capsule, but other sorts of devices or suitable implementations may be used. The in vivo device, according to some embodiments, may typically be or may be comprised of an autonomous swallowable capsule, but the device may have other shapes and need not be swallowable or autonomous. Embodiments of the device are typically autonomous, and are typically self-contained. In some embodiments, the components of the device may be enclosed within a housing or shell, e.g., capsule-shaped, oval, or having other suitable shapes. The housing or shell may be substantially transparent or semi-transparent, and/or may include one or more portions, windows or domes that may be substantially transparent or semi-transparent.

In some embodiments, the transmitter of the in vivo device may include, for example, a transmitter module or sub-unit and a receiver module or sub-unit, or an integrated transceiver or transmitter-receiver. In some embodiments, the device may communicate with an external receiving and display system to provide display of data, control, or other functions. In some embodiments, a processor may be utilized for the control of the processes and methods occurring within the device. In some embodiments, the transmitter may transmit/receive via an antenna. Control of the processes taking place within the in vivo capsule may be accomplished by a controller or a processor contained therein, or by a transmitter and/or another unit, which may include control capability.

In some embodiments, the imager in the device may be operationally connected to a transmitter. The transmitter may transmit images to, for example, an external transceiver or a transceiver/recorder (e.g., through one or more antennas), which may send the data to a processor and/or to a storage unit. The transmitter may also be capable of receiving signals/commands, for example from an external transceiver. For example, in some embodiments, the transmitter may include an ultra low power Radio Frequency (RF) high bandwidth transmitter, possibly provided in Chip Scale Package (CSP).

In some embodiments, a power source may include one or more batteries or power cells and may be internal to the device, and/or may not require coupling to an external power source.

Optionally, in some embodiments, the transmitter may include a processing unit, or processor, or controller, for example, to process signals and/or data generated by the imager. In another embodiment, the processing unit may be implemented using a separate component within the device, e.g., a controller or a processor, or may be implemented as an integral part of the imager, transmitter, or another component, or may not be needed. The processor may include a processing unit, processor or controller. The processing unit may include, for example, a CPU, a DSP, a microprocessor, a controller, a chip, a microchip, a controller, circuitry, an IC, an ASIC, or any other suitable multi-purpose or specific processor, controller, circuitry or circuit.

In some embodiments, the imager may acquire in vivo images continuously, substantially continuously, upon demand or upon a triggering event; or in a non-discrete manner, for example, not necessarily upon-demand, or not necessarily upon a triggering event or an external activation or external excitement; or in a periodic manner, an intermittent manner, or an otherwise non-continuous manner. In some embodiments, the transmitter may transmit image data continuously, upon demand or upon a triggering event, or substantially continuously, for example, not necessarily upon-demand, or not necessarily upon a triggering event or an external activation or external excitement; or in a periodic manner, an intermittent manner, or an otherwise non-continuous manner. In some embodiments, illumination source(s) may illuminate continuously, or substantially continuously, for example, not necessarily upon-demand or not necessarily upon a triggering event or an external activation or external excitement, or in a periodic manner.

An optional optical system, including, for example, one or more optical elements, such as one or more lenses or composite lens assemblies, one or more suitable optical filters, or any other suitable optical elements, may optionally be included in the device and may aid in focusing reflected light onto the imager, focusing illuminated light, and/or performing other light processing operations.

In some embodiments, the device may include one or more illumination sources, for example one or more Light Emitting Diodes (LEDs), "white LEDs", or other suitable light sources. In some embodiments, the device may include one or more illumination sources wherein the illumination sources are in a color transmission range that is narrower than "white LEDs" and may be monochromatic in certain embodiments. In certain embodiments, the color of the illumination source is selected based on the pathology sought to be detected.

A data processor may analyze the data received via external transceiver/recorder from device, and may be in communication with storage unit, e.g., transferring frame data to and from storage unit. Data processor may provide the analyzed data to monitor, where a user (e.g., a physician) may view or otherwise use the data. Monitor may include, for example, one or more screens, monitors, or suitable display units. Typically, the device may transmit image information in discrete portions. Each portion may typically correspond to an image or a frame; other suitable transmission methods may be used. In some embodiments, the image analysis and/or comparison may be performed in substantially real time. In another embodiment, the invention provides a graphical user interface, as displayed on monitor. This interface allows the user to enable more distinct viewing of the selected images at will.

Embodiments of the invention may provide various other benefits and/or advantages. Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The subject matter regarded as the invention is particularly pointed out and distinctly claimed in the concluding portion of the specification. The principles, organization, and method of operation of the system and apparatus, according to the present invention, together with objects, features, and advantages thereof; may be best understood by reference to the drawings and the following description, it being understood that these drawings are given for illustrative purposes only and are not meant to be limiting, wherein:

Figure 1:
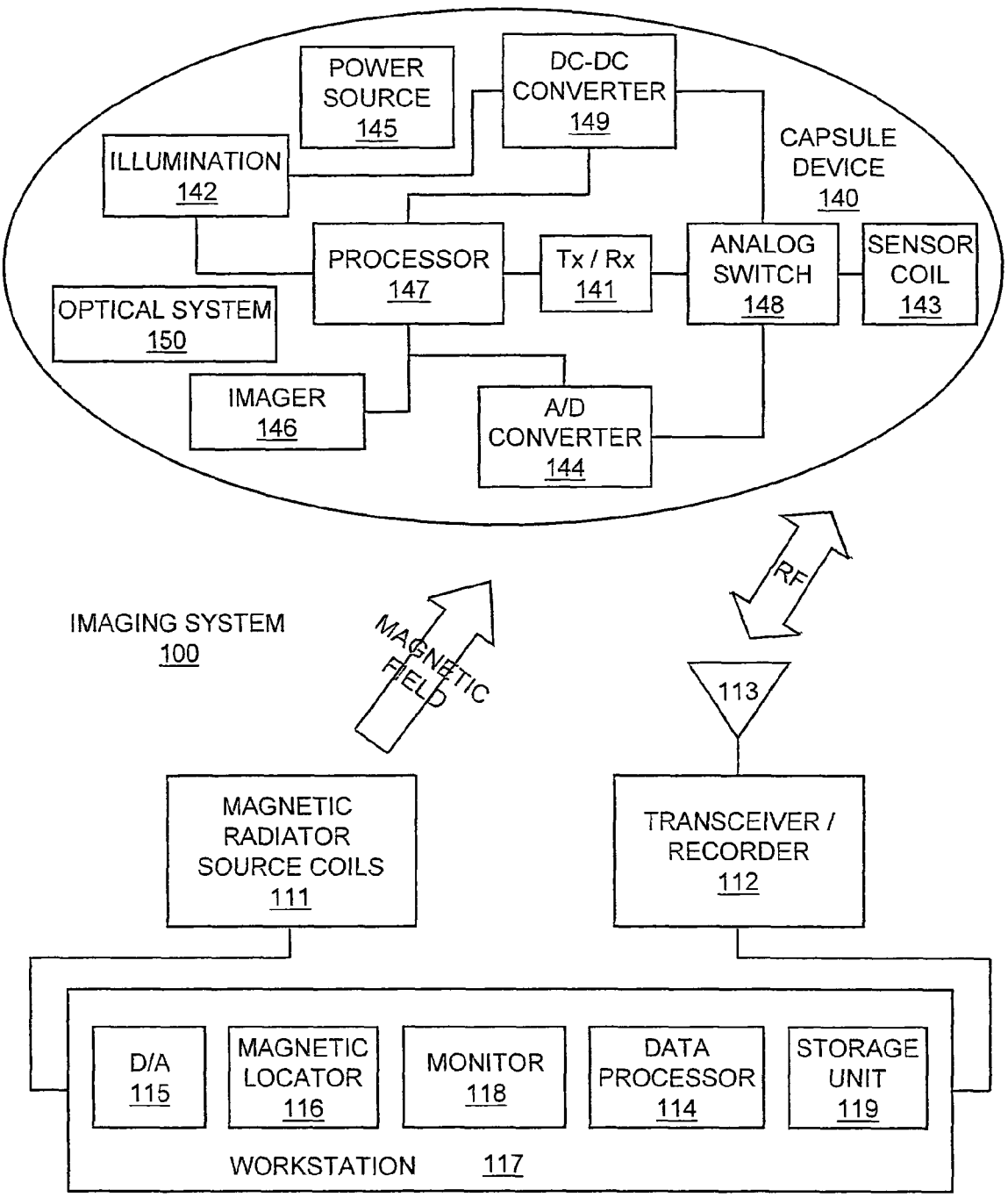
FIG. 1 is a schematic illustration of an in vivo system according to an embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Some embodiments of the present invention may be directed to an in vivo device that may be inserted into a body lumen, e.g., the gastro-intestinal (GI) tract, for example, from outside the body. Some embodiments are directed to a typically one-time use or partially single-use detection and/or analysis device. Some embodiments are directed to a typically swallowable in vivo device that may passively or actively progress through a body lumen, e.g., the gastro-intestinal (GI) tract, pushed along, for example, by natural peristalsis. Some embodiments are directed to in vivo sensing devices that may be passed through other body lumens, for example, through blood vessels, the reproductive tract, or the like. The in vivo device may be, for example, a sensing device, an imaging device, a diagnostic device, a detection device, an analysis device, a therapeutic device, or a combination thereof. In some embodiments, the in vivo device may include an image sensor or an imager and/or other suitable components. Some embodiments of the present invention may be directed to other devices, not necessarily having to do with in vivo imaging.

Devices, systems and methods according to some embodiments of the present invention, including for example in vivo sensing devices, receiving systems and/or display systems, may be similar to embodiments described in U.S. Pat. No. 5,604,531 to Iddan et al., entitled "In vivo Video Camera System", and/or in U.S. Pat. No. 7,009,634 to Iddan et al., entitled "Device for in vivo Imaging", all of which are hereby incorporated by reference in their entirety.

Devices and systems as described herein may have other configurations and/or sets of components. For example, an external transceiver/recorder unit, a processor and a monitor, e.g., in a workstation, such as those described in the above publications, may be suitable for use with some embodiments of the present invention. Devices and systems as described herein may have other configurations and/or other sets of components. Some in vivo devices may be capsule shaped, or may have other shapes, for example, a peanut shape or tubular, spherical, conical, or other suitable shapes.

Some embodiments of the present invention may include, for example, a typically swallowable in vivo device. In other embodiments, an in vivo device need not be swallowable and/or autonomous, and may have other shapes or configurations. Some embodiments may be used in various body lumens, for example, the GI tract, blood vessels, the urinary tract, the reproductive tract, or the like.

Embodiments of the in vivo device are typically autonomous and are typically self-contained. For example, the in vivo device may be or may include a capsule or other unit where all the components are substantially contained within a container, housing or shell, and where the in vivo device does not require any wires or cables to, for example, receive power or transmit information. The in vivo device may communicate with an external receiving and display system to provide display of data, control, or other functions. For example, power may be provided by an internal battery or an internal power source, or using a wired or wireless power-receiving system. Other embodiments may have other configurations and capabilities. For example, components may be distributed over multiple sites or units; and control information or other information may be received from an external source.

Devices, systems and methods in accordance with some embodiments of the invention may be used, for example, in conjunction with a device which may be inserted into a human body or swallowed by a person. However, embodiments of the invention are not limited in this regard, and may be used, for example, in conjunction with a device which may be inserted into, or swallowed by, a non-human body or an animal body. Other embodiments of the invention need not be used with in vivo imaging devices, and may be used for determining the position of a sensing probe or other object within a cavity, a tract, or some other location where it is difficult to determine the probe's position.

FIG. 1, to which reference is now made, schematically illustrates an in vivo imaging system 100 in accordance with some embodiments of the present invention. Imaging system 100 may comprise a swallowable capsule device 140, transceiver/recorder 112 that may be connected to transmitting/receiving (Tx/Rx) antenna 113 and to workstation 117, and electromagnetic radiator source coils 111 that may be connected to workstation 117. One or more components of the system may be used in conjunction with, or may be operatively associated with, the devices and/or components described herein, or with other in vivo devices in accordance with embodiments of the invention.

Device 140 may comprise an imager 146, one or more illumination sources 142, a power source 145, and a transceiver (Tx/Rx) 141. In some embodiments, an optical system 150 may be implemented to enable enhanced imaging. In some embodiments, processor 147 may be utilized for the overall control of the processes and methods occurring within device 140.

In some embodiments, device 140 may include a sensor coil assembly 143, which may comprise a set of one or more coils, and which may be used for one or more functionalities, which may be independent of each other, as will be explained in detail below, such as an electromagnetic sensor used for localization of the imaging device 140; as a part of a DC-DC voltage step-up converter 149 used for providing light sources 142 with power from power source 145 for illuminating the GI tract; and as an antenna for transceiver 141 used for transmitting images, receiving control instructions, etc. In some embodiments, device 140 may comprise an analog-to-digital (A/D) converter 144 that may be used to read the current from the electromagnetic sensor 143 for localization purposes. In some embodiments, a logical switch (such as an analog switch) 148 may be used as a means of switching between coil 143 and the functional blocks such as DC-DC converter 149, transceiver module 141, and A/D converter 144 in order to achieve its multiple purposes. However, other means of switching between various functional blocks of capsule device 140 may be used in other embodiments. Moreover, these functional blocks may not necessarily be implemented as separate modules, but may be integrated into other modules or functional blocks of device 140.

In some embodiments, device 140 may be implemented using a swallowable capsule, but other sorts of devices or suitable implementations may be used. A transceiver/recorder 112 may be located outside the body of a patient, including, or operatively associated with, for example, one or more antennas 113, or an antenna array. Additionally, electromagnetic positioning source coils 111, which are described in detail below, may be located outside the body of a patient. According to embodiments of the present invention, workstation 117 may be connected to, or in operative communication with receiver/recorder 112, antenna 113, and with electromagnetic positioning source coils 111. Workstation 117 may comprise storage unit 119, which may be or include, for example, one or more of a memory, a database, etc. or other storage systems; a processor 114, a monitor 118, an electromagnetic source locator 116, and a digital-to-analog (D/A) converter 115, which may be used to deliver the appropriate amount of current to electromagnetic source coils 111 for localization purposes. Workstation 117 may be embodied as a standalone unit or may be comprised in another unit (not shown).

Transceiver 141 may operate using wireless transmission, such as radio waves; but in some embodiments, such as those where device 140 is or is included within an endoscope, transceiver 141 may transmit/receive data via, for example, wire, optical fiber, and/or other suitable methods. Other known wireless methods of transmission may be used. Transceiver 141 may include, for example, a transmitter module or sub-unit and a receiver module or sub-unit, or an integrated transceiver or transmitter-receiver.

Device 140 typically may be or may include an autonomous swallowable capsule, but device 140 may have other shapes and need not be swallowable or autonomous. Embodiments of device 140 are typically autonomous, and are typically self-contained. For example, device 140 may be a capsule or other unit where all the components are substantially contained within a container or shell, and where device 140 does not require any wires or cables to, for example, receive power or transmit/receive information. In some embodiments, device 140 may be autonomous and non-remote-controllable; in another embodiment, device 140 may be partially or entirely remote-controllable.

In some embodiments, device 140 may communicate with an external receiving and display system, e.g., workstation 117 or monitor 118, to provide display of data, control, or other functions. For example, power may be provided to device 140 using an internal battery, an internal power source, or a wireless system able to receive power. Other embodiments may have other configurations and capabilities. For example, components may be distributed over multiple sites or units, and control information or other information may be received from an external source.

In some embodiments, device 140 may include an in vivo video camera, for example, imager 146, which may capture and transmit images of, for example, the GI tract while device 140 passes through the GI lumen. Other lumens and/or body cavities may be imaged and/or sensed by device 140. In some embodiments, imager 146 may include, for example, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In some embodiments, imager 146 in device 140 may be operationally connected to transceiver 141. Transceiver 141 may transmit images to, for example, external transceiver or transceiver/recorder 112 (e.g., through one or more antennas 143 and 113 respectively), which may send the data to processor 114 and/or to storage unit 119 of workstation 117. Transmitter 141 may also include control capability, although control capability may be included in a separate component, e.g., processor 147. Transceiver 141 may include any suitable transmitter able to transmit image data, other sensed data, and/or other data (e.g., control data) to a receiving device. Transceiver 141 may also be capable of receiving signals/commands, for example from an external transceiver. For example, in some embodiments, transceiver 141 may include an ultra low power Radio Frequency (RF) high bandwidth transmitter, possibly provided in Chip Scale Package (CSP).

In some embodiments, transceiver 141 may transmit/receive via antenna 143. Transceiver 141 and/or another unit in device 140, e.g., a controller or processor 147, may include control capability, for example, one or more control modules, processing module, circuitry and/or functionality for controlling device 140, for controlling the operational mode or settings of device 140, and/or for performing control operations or processing operations within device 140. According to some embodiments, transceiver 141 may include a receiver which may receive signals (e.g., from outside the patient's body), for example, through sensor coil 143 (acting as an antenna) or through a different antenna or receiving element. According to some embodiments, signals or data may be received by a separate receiving device in device 140.

In some embodiments, power source 145 may include one or more batteries or power cells. For example, power source 145 may include silver oxide batteries, lithium batteries, other suitable electrochemical cells having a high energy density, or the like. Other suitable power sources may be used. For example, power source 145 may receive power or energy from an external power source (e.g., an electromagnetic field generator), which may be used to transmit power or energy to in vivo device 140.

In some embodiments, power source 145 may be internal to device 140, and/or may not require coupling to an external power source, e.g., to receive power. Power source 145 may provide power to one or more components of device 140 continuously, substantially continuously, or in a non-discrete manner or timing, or in a periodic manner, an intermittent manner, or an otherwise non-continuous manner. In some embodiments, power source 145 may provide power to one or more components of device 140, for example, not necessarily upon-demand, or not necessarily upon a triggering event, or an external activation, or external excitation. Power source 145, while not shown as connected to any other module or unit within capsule device 140 in FIG. 1, should be understood as delivering power to any and all such modules or units that may require power for their operation.

Optionally, in some embodiments, transceiver 141 may include a processing unit, a processor, or a controller, for example, to process signals and/or data generated by imager 146. In another embodiment, the processing unit may be implemented using a separate component within device 140, e.g., controller or processor 147, or may be implemented as an integral part of imager 146, transceiver 141, or another component, or may not be needed. The processing unit may include, for example, a Central Processing Unit (CPU), a Digital Signal Processor (DSP), a microprocessor, a controller, a chip, a microchip, a controller circuitry, an Integrated Circuit (IC), an Application-Specific Integrated Circuit (ASIC), or any other suitable multi-purpose or specific processor, controller, circuitry or circuit. In some embodiments, for example, the processing unit or controller may be embedded in or integrated with transceiver 141, and may be implemented, for example, using an ASIC.

In some embodiments, imager 146 may acquire in vivo images continuously, substantially continuously, or in a non-discrete manner, for example, not necessarily upon demand, or not necessarily upon a triggering event or an external activation or external excitement; or in a periodic manner, an intermittent manner, or an otherwise non-continuous manner.

In some embodiments, transmitter 141 may transmit image data continuously, or substantially continuously, for example, not necessarily upon-demand, or not necessarily upon a triggering event or an external activation or external excitement; or in a periodic manner, an intermittent manner, or an otherwise non-continuous manner.

In some embodiments, device 140 may include one or more illumination sources 142, for example one or more Light Emitting Diodes (LEDs), "white LEDs", or other suitable light sources. Illumination sources 142 may, for example, illuminate a body lumen or cavity being imaged and/or sensed. An optional optical system 150, including, for example, one or more optical elements, such as one or more lenses or composite lens assemblies, one or more suitable optical filters, or any other suitable optical elements, may optionally be included in device 140 and may aid in focusing reflected light onto imager 146, focusing illuminated light, and/or performing other light processing operations.

In some embodiments, device 140 may include one or more illumination sources 142 wherein the illumination sources are in a color transmission range that is narrower than "white LEDs" and may, for example, be red, yellow, blue, green, purple, orange, infra-red, or ultra-violet in certain embodiments. Other wavelengths may be used. In some embodiments, the color of the illumination source is selected based on the pathology sought to be detected. In certain embodiments, narrowing the wavelength emitted by the illumination source 142 may assist in obtaining a better contrast. Accordingly and in another embodiment, device 140 comprises an illumination source 142 wherein the illumination source is one or more light emitting diodes, emitting light at a wavelength of between about 430 and 530 nm (Blue LED) with a peak at about 480 nm, or in another embodiment a green LED emitting light at a wavelength of between about 480 and 580 nm, with a peak at about 530 nm, or in another embodiment a red LED emitting light at a wavelength of between about 580 and 680 nm, with a peak at about 630 nm.

In some embodiments, illumination source(s) 142 may illuminate continuously, or substantially continuously, for example, not necessarily upon demand, or not necessarily upon a triggering event or an external activation or external excitement. In some embodiments, for example, illumination sources) 142 may illuminate a pre-defined number of times per second (e.g., two or four times), substantially continuously, e.g., for a time period of two hours, four hours, eight hours, or the like; or in a periodic manner, an intermittent manner, or an otherwise non-continuous manner.

In some embodiments, the components of device 140 may be enclosed within a housing or shell, e.g., capsule-shaped, oval, or having other suitable shapes. The housing or shell may be substantially transparent or semi-transparent, and/or may include one or more portions, windows or domes that may be substantially transparent or semi-transparent. For example, one or more illumination source(s) 142 within device 140 may illuminate a body lumen through a transparent or semi-transparent portion, window or dome; and light reflected from the body lumen may enter the device 140, for example, through the same transparent or semi-transparent portion, window or dome, or, optionally, through another transparent or semi-transparent portion, window or dome, and may be received by optical system 150 and/or imager 146. In some embodiments, for example, optical system 150 and/or imager 146 may receive light, reflected from a body lumen, through the same window or dome through which illumination source(s) 142 illuminate the body lumen.

According to some embodiments of the present invention, a single coil assembly 143 may be utilized for three separate and independent functionalities:
(i) an electromagnetic sensor used for localization of device 140;
(ii) a part of a DC-DC voltage step-up converter 149, which may be used, for example, for providing LED light sources 142 with power delivered from power source 145 for illuminating the GI tract; and
(iii) an antenna which may be a part of transceiver 141 used for transmitting images, receiving control instructions, etc.

According to an embodiment of the invention, a time division multiplexing scheme may be utilized for using coil assembly 143 to achieve its multiple purposes. For example, a part of the coil's duty cycle may be dedicated to the task of localizing the electromagnetic sensor coil 143, while another part may be spent stepping up the voltage in DC-DC converter 149 while supplying energy from power source 145 to light sources 142 for the illumination of the GI tract, while a third part may be used for transmission of images by transceiver 141, and yet another part of the duty cycle may be used for receiving instructions by transceiver 141 from transceiver/recorder 112 and workstation 117.

According to an embodiment of the invention, electromagnetic positioning source coils 111 may be connected to electromagnetic positioning locator 116, which may be included as part of workstation 117. In some embodiments of the invention, source coils 111 may be connected to one or more digital-to-analog (D/A) converters 115, which may be used to deliver the appropriate amounts of current to the source coils for positioning purposes. In some embodiments of the invention, D/A converters 115 may be integrated with electromagnetic locator 116, whereas in other embodiments they may comprise separate modules or units.

Data processor 114 may include a processing unit, processor or controller. The processing unit may include, for example, a CPU, a DSP, a microprocessor, a controller, a chip, a microchip, a controller circuitry, an IC, an ASIC, or any other suitable multi-purpose or specific processor, controller, circuitry or circuit.

Data processor 114 may analyze the data received via external transceiver/recorder 112 from device 140, and may be in communication with storage unit 119, e.g., transferring frame data to and from storage unit 119. Data processor 114 may provide the analyzed data to monitor 118, where a user (e.g., a physician) may view or otherwise use the data. In some embodiments, data processor 114 may be configured for real-time processing and/or for post-processing to be performed and/or viewed at a later time. In the case that control capability (e.g., delay, timing, etc) is external to device 140, a suitable external device (such as, for example, data processor 114 or external transceiver/recorder 112 having a transmitter or transceiver) may transmit one or more control signals to device 140.

Monitor 118 may include, for example, one or more screens, monitors, or suitable display units. Monitor 118, for example, may display one or more images or a stream of images captured and/or transmitted by device 140, e.g., images of the GI tract or of other imaged body lumen or cavity. Additionally or alternatively, monitor 118 may display, for example, control data, location or position data (e.g., data describing or indicating the location or the relative location of device 140), orientation data, and various other suitable data. In some embodiments, for example, both an image and its position (e.g., relative to the body lumen being imaged, relative to an external reference frame, or otherwise relative to any other reference system) or location may be presented using monitor 118 and/or may be stored using storage unit 119. Other systems and methods of storing and/or displaying collected image data and/or other data may be used.

Typically, device 140 may transmit image information in discrete portions. Each portion may typically correspond to an image or a frame; other suitable transmission methods may be used. For example, in some embodiments, device 140 may capture and/or acquire an image once every half second, and may transmit the image data to external transceiver/recorder 112. Other constant and/or variable capture rates and/or transmission rates may be used.

In some embodiments, the image analysis and/or comparison may be performed in substantially real time, for example, while device 140 is in vivo, while imager 146 acquires images, while transceiver 141 transmits image data, while transceiver/recorder 112 receives image data, and/or while workstation 117 displays in vivo images.

In another embodiment, the invention provides a graphical user interface, as displayed on monitor 118, that provides the user with the option of viewing a selected image captured by the in vivo imaging device in either regular view or in the color expanded or "enhanced" color view, e.g., in the full spectrum of visible colors. This interface allows the user to enable more distinct viewing of the selected images at will.

While every effort has been made to show the interconnections between the various functional blocks comprising the capsule device module 140, not all such connections have been shown in FIG. 1 so as not to obscure the drawing and its purpose. For example, the connections between power source 145 and all the other functional blocks that may use such power have not been shown, but may be implied. Also, no connections have been shown between optical system 150 and the rest of the system, as optical system 150 may not have electrical connections with the rest of the system, or may have electronically activated focusing features, etc., which are beyond the scope of the present invention. It should also be understood that while various functional blocks have been connected in capsule device 140 in FIG. 1 by solid lines, it should not be construed to represent the only possible implementation of the present invention, but should be viewed merely as an example for illustrative purposes, which was used to explain one possible embodiment of the invention. Likewise, it should be understood that various functional blocks in workstation 117 may not all be grouped together into one console, but may be incorporated into other devices or modules. Lastly, both capsule device 140 and workstation 117 may contain more or fewer functional blocks than shown in FIG. 1, and both may differ from the ones shown.

Dipole Fields

In a localization system, such as imaging system 100, comprised only of dipoles, m=m$\hat{m}$, where m is the magnetic dipole moment with magnitude m and direction $\hat{m}$, located at the origin. Physically, it may consist of a small current loop with m=Ia$\hat{n}$, where I is the current, a is the loop area, and $\hat{n}$ is a unit vector normal to the loop area, with a direction determined by applying the right-hand rule to the current direction. For convenience, the dipole moment will be expressed in Cartesian coordinates $$m = \hat{x}m_x + \hat{y}m_y + \hat{z}m_z \tag{1}$$

The magnetic field associated with m, written in spherical coordinates, is given by $$H = \begin{pmatrix} H_r \\ H_\vartheta \\ H_\varphi \end{pmatrix} = \frac{1}{4\pi r^3} T_d \begin{pmatrix} m_x \\ m_y \\ m_z \end{pmatrix} \tag{2}$$

where r, $\vartheta$, and $\varphi$ are the angular coordinates of the coil's location, and where $T_d$ is the dipole response matrix $$T_d(\vartheta, \varphi) = \begin{pmatrix} 2\sin\vartheta\cos\varphi & 2\sin\vartheta\sin\varphi & 2\cos\varphi \\ -\cos\vartheta\cos\varphi & -\cos\vartheta\sin\varphi & \sin\varphi \\ \sin\varphi & -\cos\varphi & 0 \end{pmatrix} \tag{2a}$$

It is seen from the above that the radiation pattern of a single dipole source is relatively simple. This is best observed for a dipole oriented along the $\hat{z}$ direction. In that case, $H_r$ behaves as cos θ and $H_\theta$ as sin θ, and both are φ-independent. Due to the circular symmetry, the $H_\varphi$ field component vanishes.

When a single coil, such as sensor coil 143, having an orientation $\hat{n}=(n_r, n_\vartheta, n_\varphi)$ is located at r=(r,θ,φ), with as yet unknown vectors $\hat{n}$ and r, the coil can measure the magnetic field component normal to its surface, f=H·$\hat{n}$. The measurement f is related to the dipoles by $$f = \frac{1}{4\pi r^3} \hat{n} T_d m \tag{3}$$

The matrix equation above provides three independent equations. They relate three measurements $f_1$, $f_2$, $f_3$ to three linearly independent excitations $m_1$, $m_2$, $m_3$ respectively, with $f_1$ due to $m_1=(1,0,0)$, $f_2$ due to $m_2=(0,1,0)$, etc. If the orientation vector $\hat{n}$ is known, then these equations may be used to determine the three unknown components of sensor coil 143 location $r=(r,\theta,\phi)$. However, if $\hat{n}$ is unknown, then the three equations may not be sufficient to determine r as at least six independent equations are required.

Quadrupole Fields

A magnetic quadrupole, such as properly arranged coils in electromagnetic radiator source coils 111, for example, can be synthesized by positioning two magnetic dipoles (loops or coils) in parallel, excited with opposite polarity. This may be realized by using two identical coils and controlling their polarity by the phase of their currents. Let $m_q = \hat{m}_q m_q$ be the single dipole moment, and let $d = \hat{d} d$ be the vector connecting the negatively polarized single dipole ($-m_q$) and the positively polarized one ($+m_q$). The quadrupole plane is defined as the plane containing the two dipoles and hence containing also the two vectors $m_q$ and d. The system is presented schematically in FIG. 2. The observation point of FIG. 2 may represent sensor coil 143 in system 100 of FIG. 1. Throughout the description below it is to assumed that the physical dimensions of each dipole and the length of d are much smaller than the distance at which the quadrupole is observed.

Magnetic quadrupoles may be synthesized using identical and oppositely polarized simple magnetic dipoles (coils). We define the Quadrupole plane as the plane containing the two dipoles. For all the subfigures here, the quadrupole plane is the paper plane. The single dipole moment is $m_q$ and the dipoles separation is d. The large arrows show the true electric current direction in the coils. (a) General construction. (b) The optimal case is when $m_q$ and d are mutually orthogonal. (c) A quadrupole obtained by interchanging the directions of d and m. Although constructed differently (different orientation of the coils!) the field of this quadrupole is identical to the field of the quadrupole shown in (b).

The field pattern and the associated degrees of freedom of the quadrupole may be first studied by obtaining the magnetic potential $\Phi_q(r)$ associated with the quadrupole. The magnetic filed may be obtained via $H = -\nabla \Phi_q$. Let $r_1$ and $r_2$ be the distances from the negative and positive magnetic dipoles to the observation point (see FIG. 2). Then $$\Phi_q(r) = \frac{m_q}{4\pi} \cdot \left( \frac{\hat{r}_1}{|r_1|^2} - \frac{\hat{r}_2}{|r_2|^2} \right) \tag{4}$$

where $\hat{r}_{1,2} = r_{1,2}/|r_{1,2}|$ a unit vector pointing in the direction of $r_{1,2}$. However, $$r_{1,2} = r \mp d/2, \Rightarrow |r_{1,2}| = \sqrt{r^2 + |d|^2 \mp r \cdot d} \approx \sqrt{r^2 \mp r \cdot d} \tag{5}$$

Figure 2A:
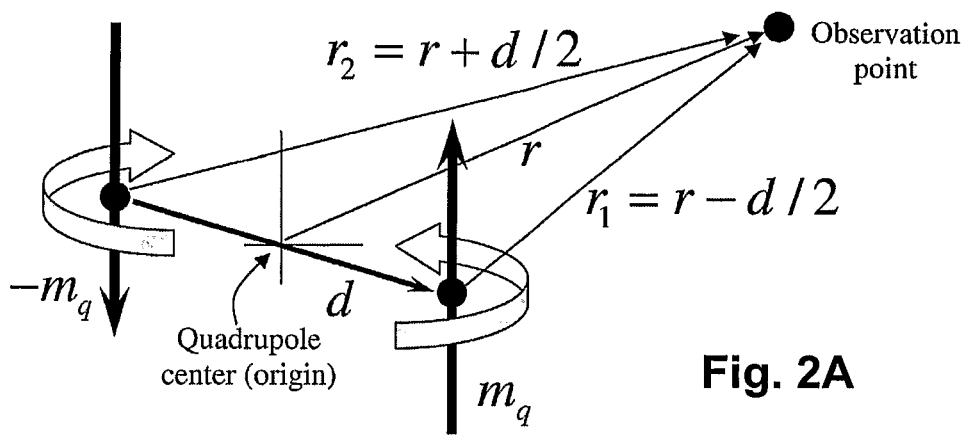
FIG. 2 is a schematic depiction of synthetic magnetic quadrupoles using identical and oppositely polarized simple magnetic dipole coils according to an embodiment of the present invention.
Figure 2B:
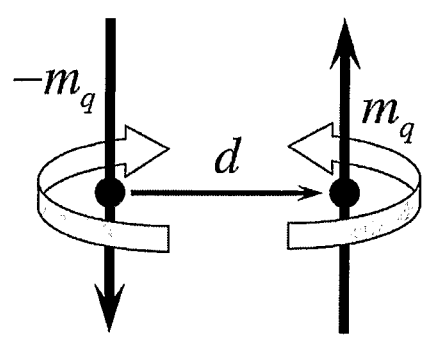
Figure 2C:
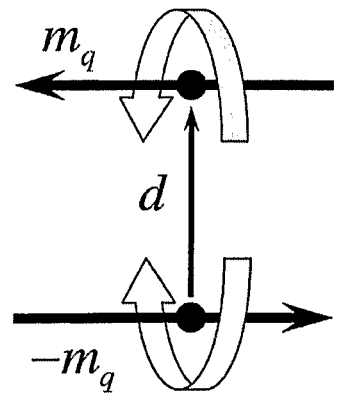

In the above, r is the length of the vector r. In Equation (5) terms of the order of $(d/r)^2$ or smaller were neglected. Substituting Equation (5) into Equation (4) using the Taylor series expansion $(1-x)^{-3/2} \approx 1 + 3x/2$ and keeping the terms up to the order of d/r, Equation (4) reduces to $$\Phi_q(r) = -\frac{m_q \cdot d}{4\pi r^3} + \frac{3 m_q d}{4\pi r^3} (\hat{m}_q \cdot \hat{r})(\hat{d} \cdot \hat{r}) \tag{6}$$

where $\hat{r}$ is a unit vector pointing from the origin (quadrupole center) to the observer located at $r = \hat{r} r$. Equation (6) discloses the quadrupole structures relevant to some embodiments of the present invention. If $m_q \cdot d \neq 0$, an additional isotropic term is present. This term, having an isotropic structure (that is depending only on r), cannot contribute location information. Therefore, in order to minimize unnecessary magnetic field components that do not contribute to solving of the localization problem, it is possible, according to embodiments of the present invention, to employ only quadrupoles for which the terms $m_q$ and d are mutually perpendicular, so that $m_q \cdot d = 0$ and the "structure-less" field is eliminated. These quadrupoles are shown in FIGS. 2 (*b*) and (*c*). The potential expressed in Equation (6) is invariant under the interchange of $m_q$ and d. For the case of orthogonal $m_q$ and d this transformation represents a rotation by 90° around an axis perpendicular to the quadrupole plane that contains the two dipoles. Therefore, according to embodiments of the present invention, the quadrupoles presented in FIGS. 2(*b*) and (*c*) possess identical fields.

According to embodiments of the present invention and based on the above analysis, there are five quadrupole configurations that may generate linearly independent fields, including geometries in which $m_q$ and d are parallel, but there are only three linearly independent quadrupoles that can contribute efficiently to solving the localization problem. Their $(m_q, d)$ vector pairs are given by $(\hat{z},\hat{x})$, $(\hat{y},\hat{x})$, $(\hat{z},\hat{y})$. These pairs also directly identify the corresponding quadrupole planes.

The quadrupole magnetic fields may be obtained by substituting the specific choice for $(m_q, d)$ in the potential and operating with $-\nabla$. According to embodiments of the present invention, the quadrupole moment may be defined as $Q_{uv} = m_q d$ where $m_q$ and d are parallel to u and v axes, respectively. Then $$H = \begin{pmatrix} H_r \\ H_\theta \\ H_\phi \end{pmatrix} = \frac{3}{8\pi r^4} T_q \begin{pmatrix} Q_{xy} \\ Q_{xz} \\ Q_{yz} \end{pmatrix} \tag{7}$$

where $T_q$ is the quadrupole response matrix $$T_q(\theta, \phi) = \begin{pmatrix} 3\sin^2\theta \cdot \sin(2\phi) & 3\sin(2\theta) \cdot \cos\phi & 3\sin(2\theta) \cdot \sin\phi \\ -\sin(2\theta) \cdot \sin(2\phi) & -2\cos(2\theta) \cdot \cos\phi & -2\cos(2\theta) \cdot \sin\phi \\ -2\sin\theta \cdot \cos(2\phi) & 2\cos\theta \cdot \sin\phi & -2\cos\theta \cdot \cos\phi \end{pmatrix} \tag{7a}$$

From the comparison of the matrix Equation of (7a) to the dipole Equations (2)-(2a) it follows that:
(i) The quadrupole field decreases as $r^{-4}$, which is one power of r faster than the dipole field; and
(ii) The quadrupole field pattern is more complex than the dipole field. For example, for the $Q_{xz}$ excitation, i.e. dipoles oriented along $\hat{z}$, the $H_r$ pattern is of the form $\sin(2\theta) \cdot \cos \phi$, as compared to the single $\hat{z}$-oriented dipole case, where $H_r$ depends on $\cos \theta$ only. This added complexity actually provides the additional information needed to solve the localization problem.

Localization Using Synthetic Source of Quadrupoles and Dipoles

According to embodiments of the present invention, an extended source configuration may be used, as depicted in FIG. 3, which is a schematization of the extended source approach, where (a) shows a pair of coils that can synthesize a monopole if the coils currents $I_1, I_2$ possess the same phase, or a quadrupole if they are in opposite phases; (b) shows the extended source consisting of at least three pairs of coils shown in (a), mounted so as to provide the required orthogonal multipoles $m_x$, $m_y$, $m_z$ (in phase excitations) and $Q_{xy}$, $Q_{xz}$, $Q_{yz}$ (anti-phase excitations)—note that this configuration is slightly non-symmetric with respect to the origin of the cartesian coordinate system; and (c) shows a symmetric construction.

Figure 3A:
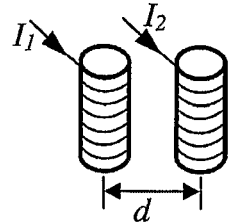
FIG. 3 is a schematic illustration of an extended magnetic source approach according to an embodiment of the present invention.
Figure 3B:
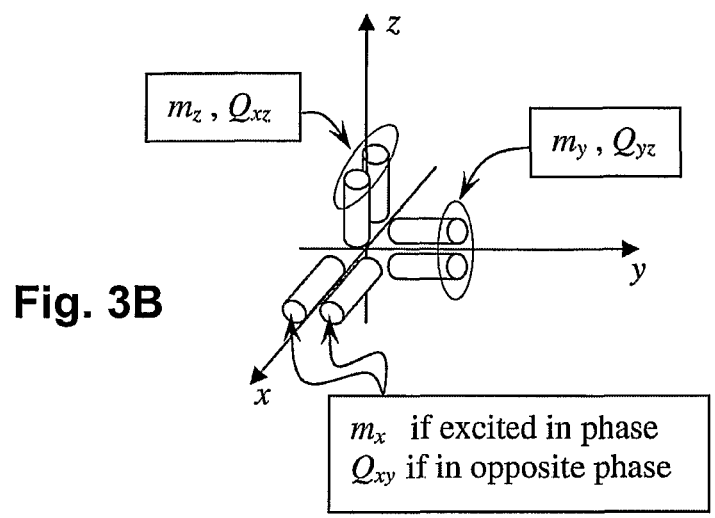
Figure 3C:
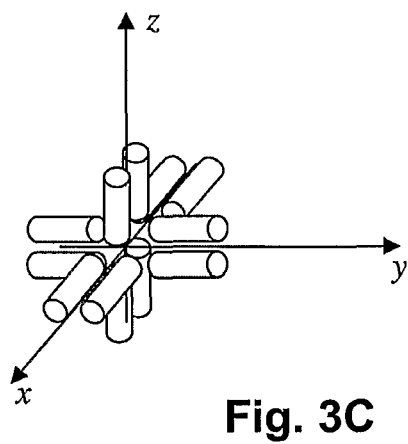

A set of three quadrupoles $Q_{xy}$, $Q_{xz}$, $Q_{yz}$, each comprising a pair of simple coils, may be mounted on the source coordinate system. Each single pair may be excited as a quadrupole if the corresponding coils are fed by currents with opposite directions or as a twice stronger dipole if the currents are in-phase, as depicted in FIG. 3(a). The extended source configuration is illustrated in FIG. 3(b) depicting a non-symmetric version and FIG. 3(c) depicting a symmetric version, which reflects the configuration of source coils 111 of FIG. 1 according to embodiments of the present invention. Thus, the set of three Equations in (3) may be obtained by this new extended source if each coil pair is excited as monopole (in-phase currents). At a further stage, the coil pairs may be excited as quadrupoles by supplying them with currents with opposite phases, following exactly the same steps discussed in the Dipole fields section (supra). Sensor coil 143 measurement g related to the quadrupole excitation may be expressed as $$g = \frac{3}{8\pi r^4} \hat{n} T_q Q, \ Q = \begin{pmatrix} Q_{xy} \\ Q_{xz} \\ Q_{yz} \end{pmatrix} \quad (8)$$

that actually provides three independent equations, which relate three measurements $g_1$, $g_2$, $g_3$ to three linearly independent excitations $Q_1$, $Q_2$, $Q_3$ respectively, with $g_1$ due to $Q_1 = (1,0,0)$, $g_2$ due to $Q_2=(0,1,0)$, etc. This set of three Equations, together with the set in Equation (3), provide six independent equations, from which the six unknown parameters of sensor coil 143 position r and orientation $\hat{n}$ can be obtained.

Solving the equations according to embodiments of the present invention, it is assumed that the initial location and orientation of sensor coil 143 are known and given by $r_0=(r_0, \theta_0, \phi_0)$ and $\hat{n}_0=(n_{r,0},n_{\theta,0},n_{\phi,0})$, respectively. The corresponding field readings associated with the linearly independent dipole excitations $m_i$ and quadrupole excitations $Q_i$ are given by $f_{0,i}$ and $g_{0,i}$ respectively (i=1, 2, 3), which satisfy the following set of six Equations, resulting from equations (3) and (8):

$$f_{0,i} = \frac{1}{4\pi r_0^3}\hat{n}_0 T_d(\theta_0, \phi_0)m_i, \ g_{0,i} = \frac{3}{8\pi r_0^4}\hat{n}_0 T_q(\theta_0, \phi_0)Q_i, i=1,2,3. \quad (9)$$

The matrices $T_d$ and $T_q$ depend only on the direction and orientation ($\theta$ and $\phi$) of dipole and quadrupole source coils 111 with respect to sensor coil 143 location.

According to embodiments of the present invention, when sensor coil 143 has changed its location and orientation from a first, known location and orientation $r_0$, $\hat{n}_0$ to an unknown second location and orientation $r_1=(r_1,\theta_1,\phi_1)$, $\hat{n}_1=(n_{r,1},n_{\theta,1},n_{\phi,1})$, the corresponding field readings have changed as well, and are given by $f_{1,i}$ and $g_{1,i}$ for the same dipole and quadrupole excitations of equation (9). They are related by $$f_{1,i} = \frac{1}{4\pi r_1^3}\hat{n}_1 T_d(\theta_1, \phi_1)m_i, \ g_{1,i} = \frac{3}{8\pi r_1^4}\hat{n}_1 T_q(\theta_1, \phi_1)Q_i, i=1,2,3. \quad (10)$$

According to embodiments of the present invention, equation (10) may be solved for the new location and orientation vectors $r_1$, $\hat{n}_1$ given the corresponding field readings $f_{1,i},g_{1,i}$. Since the equations are highly nonlinear, a perturbation solution approach may be taken according to embodiments of the present invention. In support of this approach, the variations in the field readings due to the movement of sensor coil 143 may be defined as the following:

$$f_{1,i}=f_{0,i}+\delta f_i, g_{1,i}=g_{0,i}+\delta g_i \quad (11)$$

Assuming that $r_1$, $\hat{n}_1$ are very close to $r_0$, $\hat{n}_0$, the variations in the orientation and the location related quantities may be defined as $$r_1=r_0+\delta r; \hat{n}_1=\hat{n}_0+\delta \hat{n}, T_{d,1}=T_{d,0}+\delta T_d, T_{q,1}=T_{q,0}+\delta T_q \quad (4)(12)$$

where $T_{d,k}=T_d(\theta_k,\phi_k)$, k=0,1 and the same applies for $T_{q,k}$. Approximating to the first order results in the following:

$$\delta T_d \approx \partial_\theta T_d(\theta,\phi)|_{\theta_0,\phi_0}\delta\theta + \partial_\phi T_d(\theta,\phi)|_{\theta_0,\phi_0}\delta\phi \quad (12a)$$

$$\delta T_q \approx \partial_\theta T_q(\theta,\phi)|_{\theta_0,\phi_0}\delta\theta + \partial_\phi T_q(\theta,\phi)|_{\theta_0,\phi_0}\delta\phi \quad (12b)$$

where $$\delta\theta=\theta_1-\theta_0, \delta\phi=\phi_1-\phi_0. \quad (12c)$$

Likewise, $$r_1^{-n} \approx r_0^{-n}(1-nr_0^{-1}\delta r). \quad (12d)$$

By substituting these definitions into Equation (10), keeping the terms up to the first order only, and using Equation (9), the linearized set of Equations for the six unknowns $\delta r=(\delta r, \delta\theta,\delta\phi)$, $\delta\hat{n}=(\delta\hat{n}_r,\delta\hat{n}_\theta,\delta\hat{n}_\phi)$ is thus obtained as $$-12\pi r_0^2 f_{0,i}\delta r + [\hat{n}_0\partial_\theta T_d(0)m_i]\delta\theta + [\hat{n}_0\partial_\phi T_d(0)m_i]\delta\phi + \delta\hat{n}T_d(0)m_i = 4\pi r_0^3 \delta f_i \quad (13a)$$

$$-\frac{32}{3}\pi r_0^3 g_{0,i}\delta r + [\hat{n}_0\partial_\theta T_q(0)Q_i]\delta\theta + [\hat{n}_0\partial_\phi T_q(0)Q_i]\delta\phi + \delta\hat{n}T_q(0)Q_i = \frac{8}{3}4\pi r_0^4\delta g_i \quad (13b)$$

where i=1, 2,3. The notation $\partial_a T_p(0)=\partial_a T_p(\theta,\phi)|_{\theta_0,\phi_0}$ was used for a=$\theta,\phi$ and p=d,q. Since the matrices $T_d,T_q$ are known analytically, their derivatives may be obtained in a straightforward manner.

Improving the First Order Solution by Iterations

The first order approximation obtained by solving Equations (13a)-(13b) may be improved by applying an iterative approach. $r_0$, $\hat{n}_0$ may be viewed as a crude initial guess for the desired solution $r_1$, $\hat{n}_1$ of Equation (10). Once $\delta r$, $\delta\hat{n}$ are obtained, they may be used as an improvement for the initial guess, and the process may continue iteratively until a desired result is achieved. This process may be outlined as the following:

1. Get the location and the orientation $r_0$, $\hat{n}_0$, and the corresponding field readings $f_{0,i},g_{0,i},i=1,2,3$ with $r_0$, $\hat{n}_0$ used as first guess for the unknown $r_1$, $\hat{n}_1$;
2. Get field readings $f_{1,i},g_{1,i}$ at the unknown $r_1$, $\hat{n}_1$;
3. Set iteration counter j=1;
4. $\delta f_i=f_{1,i}-f_{0,i}, \delta g_i=g_{1,i}-g_{0,i}$, i=1,2,3;

5. Solve Equations (13a)-(13b) for δr, δn̂ as per comment (i) below;
6. Obtain estimations for $r_1$, $\hat{n}_1$ via: $r_1^{(j)}=r_0+\delta r$, $\hat{n}_1^{(j)}=\hat{n}_0+\delta\hat{n}$;
7. Re-normalize $\hat{n}_1^{(j)}$; set $\hat{n}_1^{(j)}$ a $\hat{n}_1^{(j)}/P\hat{n}_1^{(j)}P$ as per comment (ii) below;
8. Check stop criteria as per comment (iii) below; if not reached, continue:
9. Set $r_0=r_1^{(j)}$, $\hat{n}_0=\hat{n}_1^{(j)}$;
10. Compute field readings $f_{0,i}, g_{0,i}$ for the new $r_0$, $\hat{n}_0$ using Equation (9);
11. j a j+1, go to step #4.

It should be noted that:
(i) Sometimes the 6×6 matrix equation in step #5 above is ill-conditioned. Therefore, in applications, according to some embodiments, one should invoke least-square solution techniques (e.g., Penrose inverse).
(ii) Formally, the normalization in step #7 may not be needed. However, it is defined as a unit vector whose length should be 1. Numerical errors may cause its length to deviate slightly from 1, thus introducing an effective "gain" into equations (9)-(10), which sometimes causes the solution to diverge quickly. Normalization may solve this problem.
(iii) The iterative process is stopped at step #8 above if the corresponding δr,δn̂ are sufficiently small, or if the iteration index j reaches a pre-set limit.
(iv) The only "true" data, read from the outside world, are the quantities $r_0$, $\hat{n}_0$, $f_{0,i}, g_{0,i}$, and $f_{1,i}, g_{1,i}$ in the input steps #1 and #2. The field readings computed in step #10 are "synthetic"; they are obtained by assuming that the sources of the magnetic fields are indeed described correctly by Equation (9).

Reconstructing a Trajectory

In most applications according to embodiments of the present invention the goal is to determine a trajectory made by sensor coil 143, when the only given data is the initial location $r_0$, the corresponding field readings $f_{0,i}, g_{0,i}$, i=1, 2, 3, and a set of field readings $f_{k,i}, g_{k,i}$, i=1, 2, 3, k=1, ... M taken at M unknown points $r_k$ with orientations $\hat{n}_k$ along the unknown trajectory. The trajectory reconstruction may be achieved by applying the following algorithm:
1. Substitute the known initial location $r_0$ and field readings $f_{0,i}, g_{0,i}$, i=1, 2, 3 into to Equation (9) and solve it for the initial location $\hat{n}_0=\hat{n}$. Note that these Equations are linear with respect to n̂ and may therefore be solved easily. In fact, the system in Equation (9) provides two sets of three Equations each, for the 3 unknowns of $\hat{n}_0$ (one set uses the f readings and the second uses the g readings). It is therefore an over-determined system. Choose to solve either set, or solve both sets for stabilization;
2. Set trajectory point counter: do k=1,K,M
3. Set
   (a) $(r_0, \hat{n}_0)=(r_{k-1}, \hat{n}_{k-1})$,
   (b) $(f_{0,i}, g_{0,i})=(f_{k-1,i}, g_{k-1,i})$, i=1,2,3,
   (c) $(f_{1,i}, g_{1,i})=(f_{k,i}, g_{k,i})$, i=1,2,3;
4. Use the algorithm in Improving the first order solution by iterations section (supra) to obtain an estimation for $(r_1, \hat{n}_1)$;
5. Set $(r_k, \hat{n}_k)=(r_1, \hat{n}_1)$
6. k a k+1, go to step #3

The algorithm properties of accuracy and convergence rates, both under "ideal" data (i.e. field measurements with no noise), and noisy data are outlined below. In actual implementations according to some embodiments of the present invention, dipole and quadrupole excitations are performed with the following parameters: in a simulation according to embodiments of the invention, all source coils 111 had a radius of 1.5 mm, number of turns N=30, and current I=10 Amp. The simulated distance between the coils was d=8 mm (see FIGS. 2, 3). According to other embodiments of the invention, smaller current may be fed to electromagnetic radiator source coils 111, as long as sufficient signal-to-noise ratio at sensor 143 is maintained. Alternatively, higher current may be fed through source coils 111, if the physical coil parameters are properly selected. Clearly, any specific set of values that leads to the same dipole and quadrupole moments would lead to exactly the same fields.

Reconstruction from Field Readings without Noise

Figure 4:
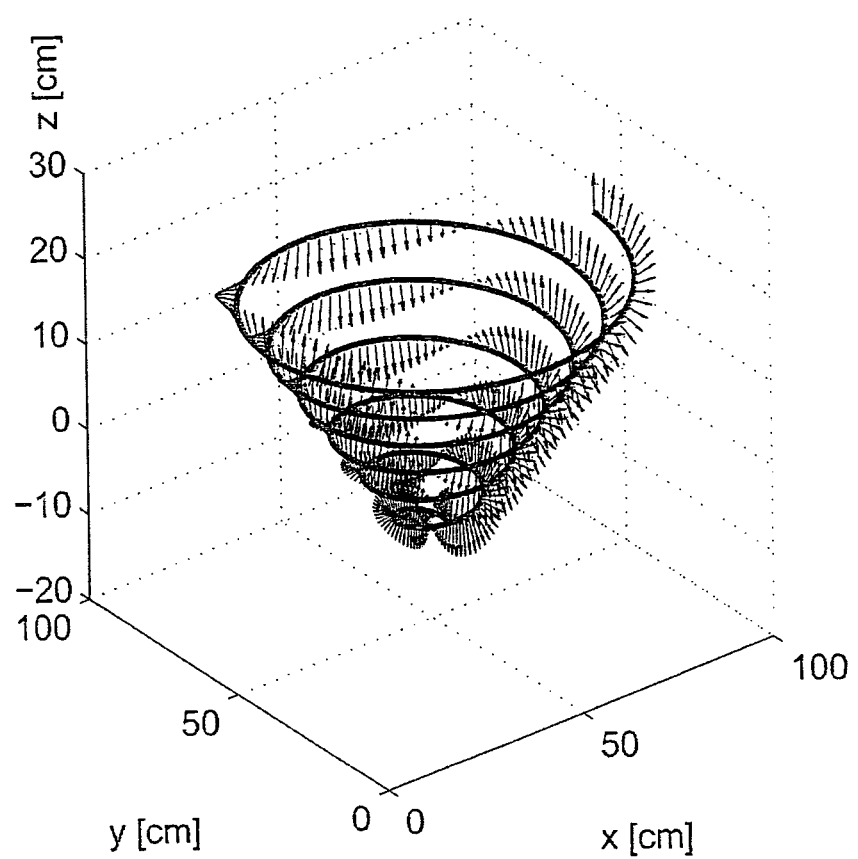
FIG. 4 is a schematic illustration of the synthetic trajectory of the device in an in vivo lumen according to an embodiment of the present invention.

In order to test the algorithm according to embodiments of the invention, a sensor coil to 143 trajectory shown in FIG. 4 was synthesized. Location of sensor coil 143 is shown by the thick spiral line. Its orientation is shown by the thinner arrows, which are normal to the plane of the coil loops. Thus, sensor coil 143 travels along a diverging spiral, and at the same time it rotates around one of its "secondary" axis. The trajectory starting point is at the bottom of the spiral, at the Cartesian coordinates of $(x_0,y_0,z_0)=(55,50,-10)$ cm. The initial spiral radius is 5 cm, and it gradually increases at a rate of 6.28 cm per turn. At the trajectory endpoint (after 6 turns) the local curvature is 42.68 cm. The z coordinate of the trajectory increases continuously at a rate of 5 cm per turn. The trajectory endpoint coordinate is $(x_e,y_e,z_e)=(92.68,50, 20)$ cm.

Figure 5:
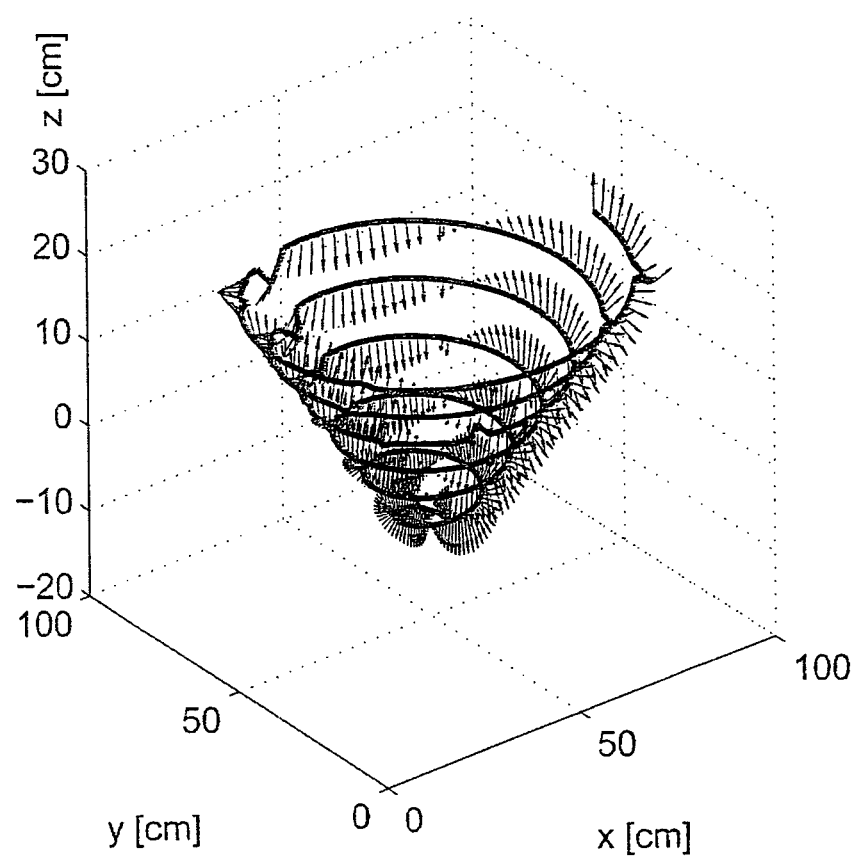
FIGS. 5-8 are schematic depictions of reconstructed trajectories using various frame rates and various number of iterations per point according to an embodiment of the present invention.

According to embodiments of the present invention and using Equations (3) and (8), the field readings data f, g were computed along this trajectory. Then they were used in the algorithm described herein in order to reconstruct the trajectory. In the first reconstruction experiment, data were taken every 4° along the spiral, which corresponds to frame rates of 1 frame per 0.35 cm at the bottom, and 1 frame per 3 cm at the spiral top. The total number of frames was 540. FIG. 5 shows the reconstructed trajectory using 1 frame per 4° (1 frame per 0.35 cm at the bottom, and 1 frame per 3 cm at the top). The number of iterations was fixed to $j_{max}=3$; see stop criteria in Improving the first order solution by iterations section (supra). The reconstruction quality in this example is reasonable and the algorithm exhibits a "self-healing" property: in several locations along the trajectory the reconstruction deviates from the original trajectory, but it converges back within the next few points. This behavior has been observed quite consistently, according to some embodiments, when more than 2 iterations were used. This behavior has been observed quite consistently, but only when more than 2 iterations were used. This is further demonstrated in the next test examples (infra).

In the next tests according to embodiments of the invention, the same synthetic trajectory of FIG. 4 was used, but with field readings taken every 6° along the spiral. The corresponding frame rates were 1 frame per 0.525 cm at the bottom, and 1 frame per 4.5 cm at the spiral top. The total number of frames was 360.

Figure 6:
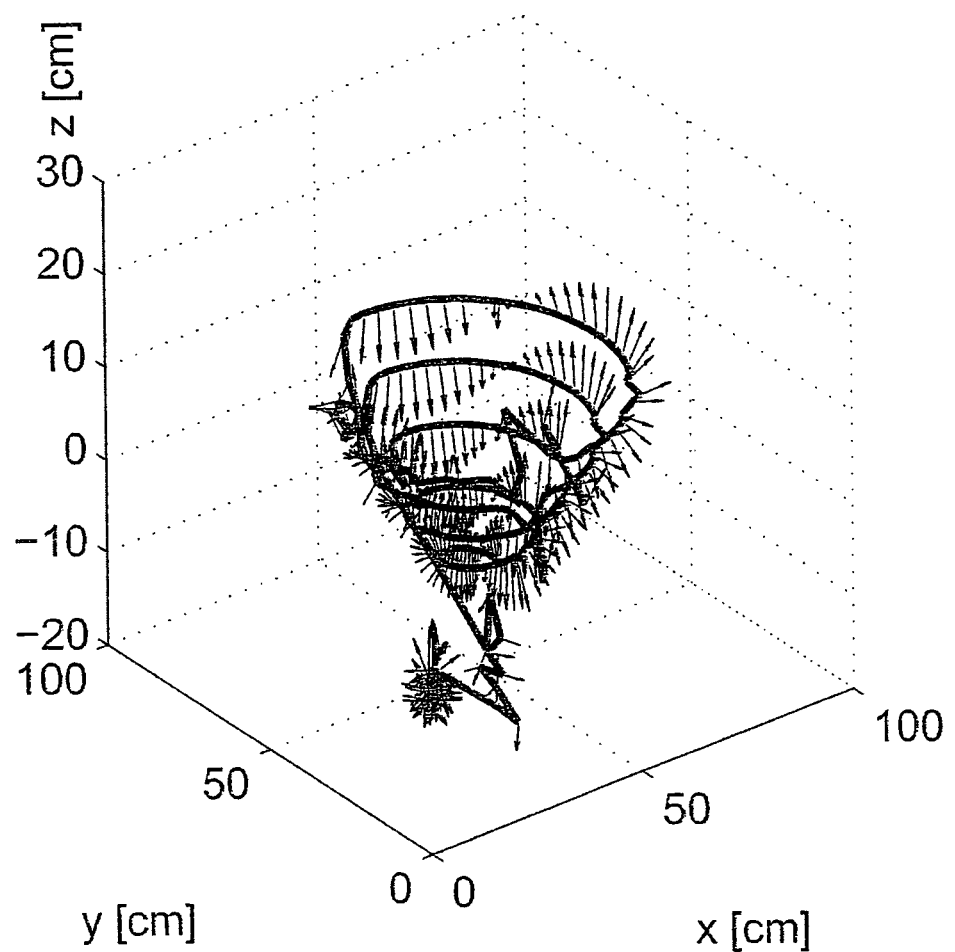
Figure 7:
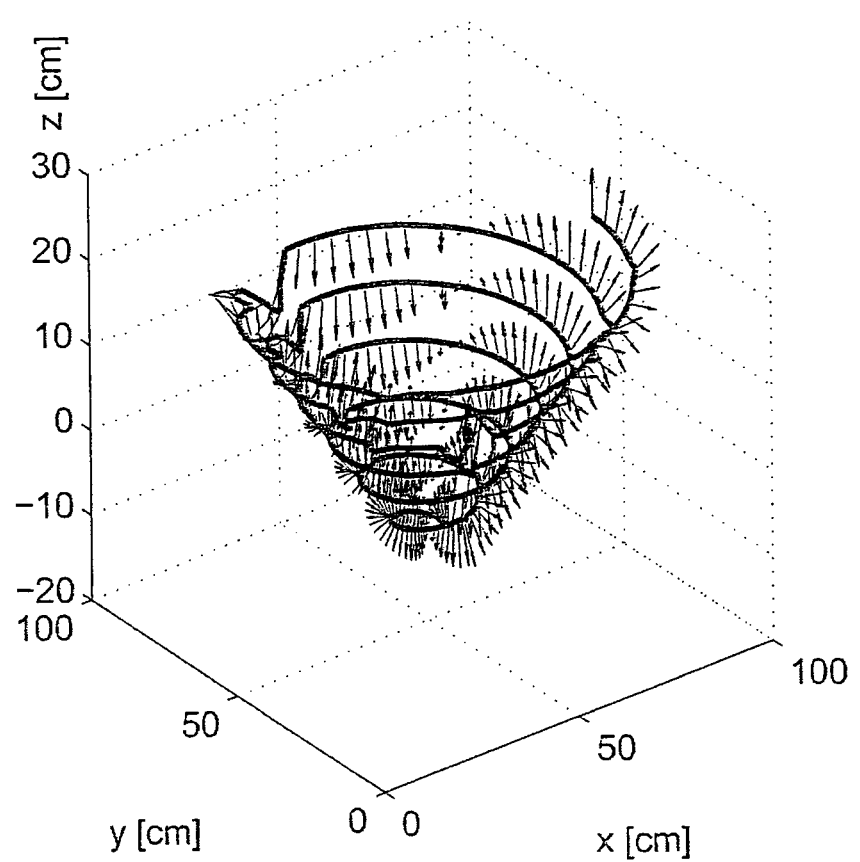
Figure 8:
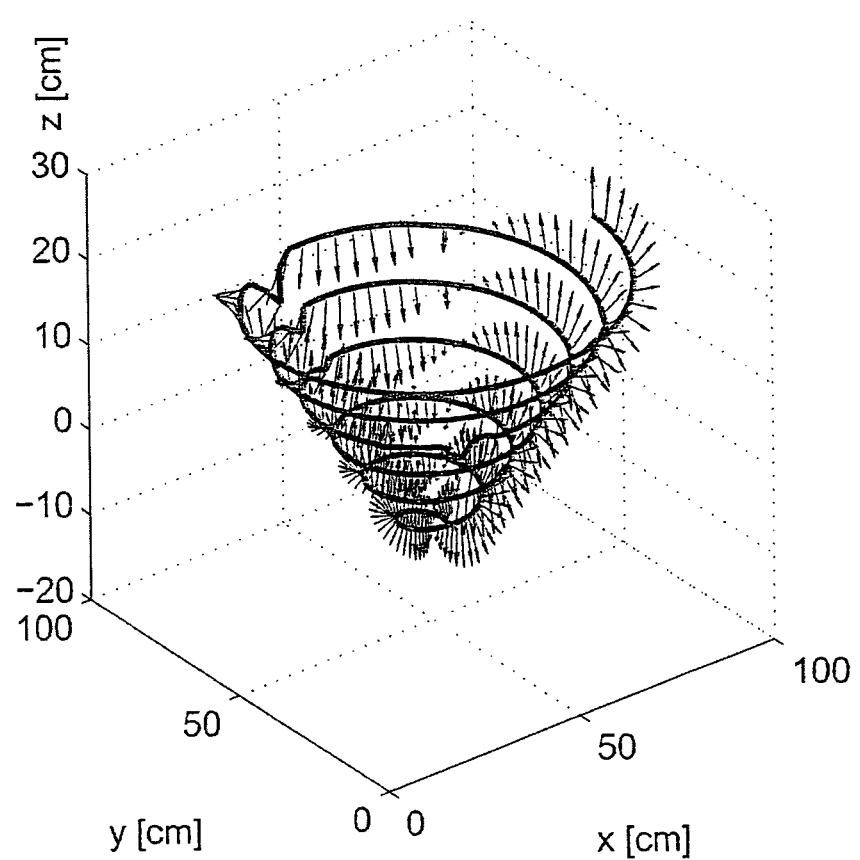

FIGS. 6, 7, and 8 show the reconstructed trajectory using this data, with 2, 3, and 7 iterations per point. FIG. 6 shows the reconstructed trajectory using 1 frame per 6° (1 frame per 0.525 cm at the bottom, and 1 frame per 4.5 cm at the top), and 2 iterations per point. FIG. 7 shows the reconstructed trajectory using frame rate as in FIGS. 6, and 3 iterations per point. FIG. 8 shows the reconstructed trajectory using frame rate as in FIGS. 6, and 7 iterations per point. A gradual improvement may be seen as the number of iterations increases. The numerical experiments show that the reconstruction quality "saturates" at 5-7 iterations. Beyond the 7-th iteration the reconstruction quality is practically invariant.

For a global measure of the algorithm convergence properties, two figures of merit may be defined:

$$E = M^{-1} \sum_{k=1}^{M} \|r_k - r_k^{rec}\|, \sigma = \sqrt{m^{-1} \sum_{k=1}^{M} \|r_k - r_k^{rec}\|^2} \quad (14)$$

where $r_k$ and $r_k^{(rec)}$ are the original and reconstructed trajectories, respectively (k=1,K,M).

Figure 9:
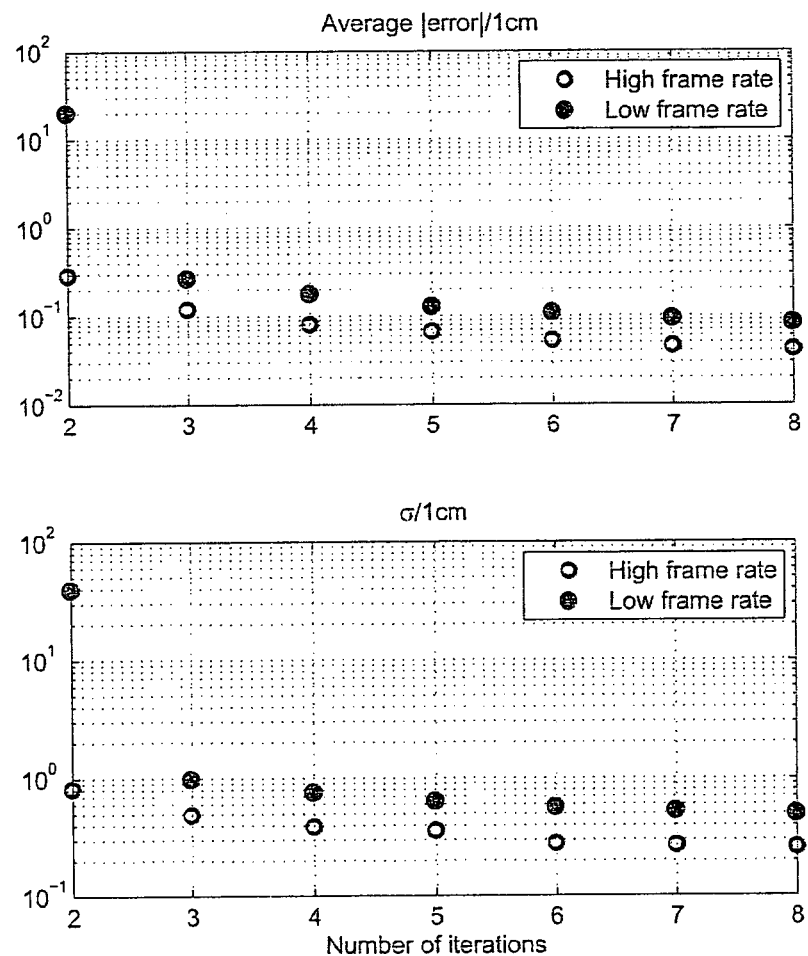
FIG. 9 is a graphic depiction of a synthetic trajectory algorithm error convergence according to an embodiment of the present invention.

FIG. 9 shows the results for both frame rates vs. the number of iterations. It may be seen, practically, that, according to some embodiments, there is no need to go beyond the 5-th iteration for both frame rates. Other numbers of iterations are possible. It may be seen, practically, that there is no need to go beyond the 5-th iteration for both frame rates. As expected, higher frame rates give better reconstruction quality. However, when saturation is achieved (beyond the 5-th iteration), both frame rates yield average deviations well below 1 cm. The algorithm convergence was tested with the global error measures in Equation (14), and for the two frame rates discussed in the text.

Reconstruction from Noisy Data

According to embodiments of the invention, the field readings $f_{k,i}, g_{k,i}$ may practically be obtained from the voltage developed across sensor coil 143 ports. This relation is given by $V_{k,i} = -j\omega\mu aN f_{k,i}$ and $V_{k,i} = -j\omega\mu aN g_{k,i}$ for the dipole and quadrupole excitations, respectively, where $\omega$ is the field frequency, a is the loop area, and N is the number of loops in sensor coil 143. An additive noise model is assumed in the measured voltages, which translates directly to additive noise in the corresponding field readings. By setting $\Delta H = V_{noise}/(-j\omega\mu aN)$, the noise at the level of the field reading may be modeled via $$f_{k,i} a f_{k,i} + \Delta H_{k,i}, g_{k,i} a\ g_{k,i} + \times H_{k,i} \quad (15)$$

where $\Delta H_{k,i}$ is a random variable with normal distribution, average 0 and standard deviation $\sigma_H$.

Figure 10:
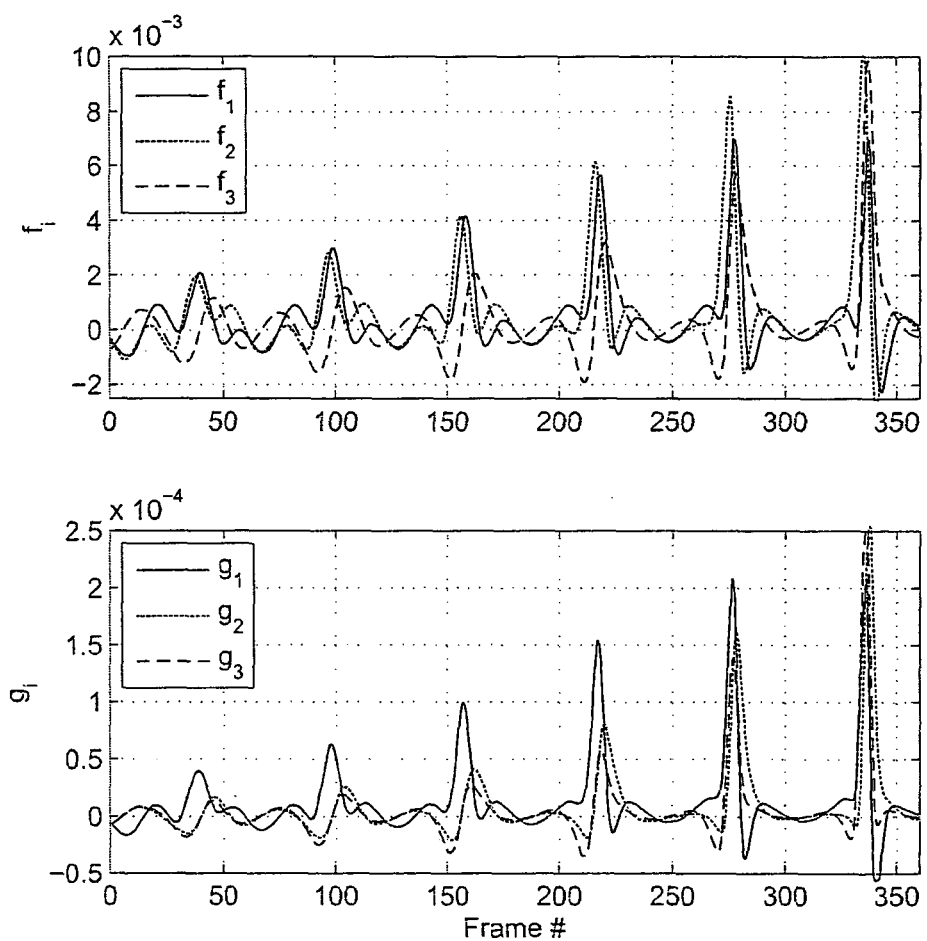
FIG. 10 is a graphic depiction of a magnetic field readings taken at low frame rate according to an embodiment of the present invention.
Figure 11:
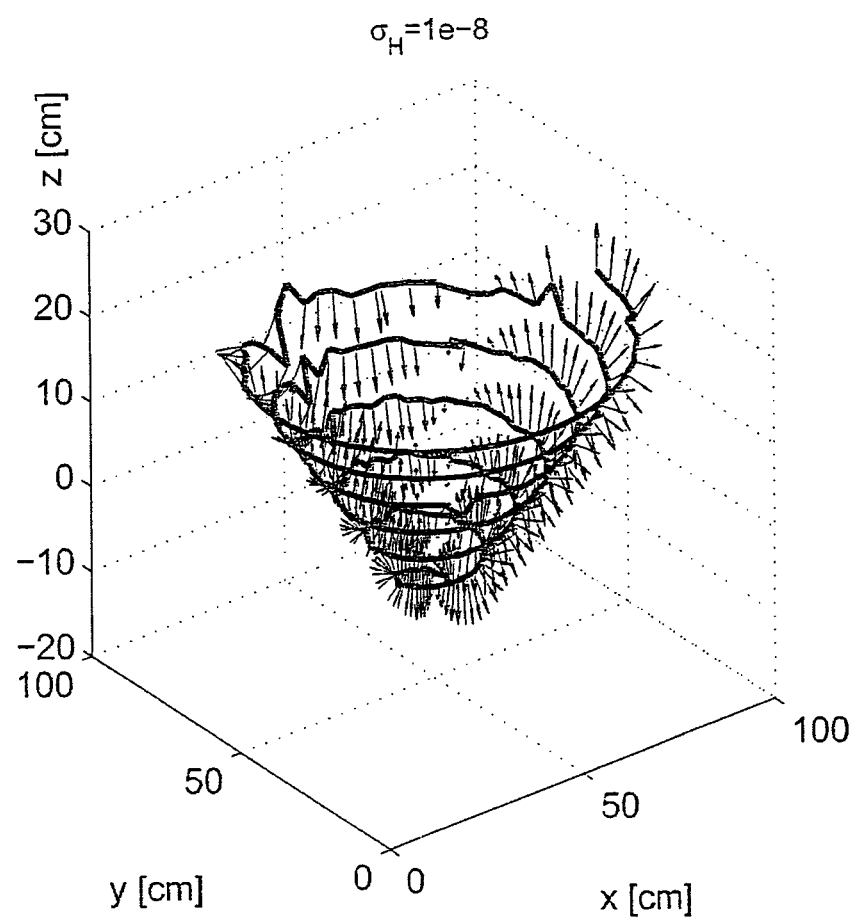
FIGS. 11-14 are schematic depictions of reconstructed trajectories with various levels of noise according to an embodiment of the present invention.
Figure 12:
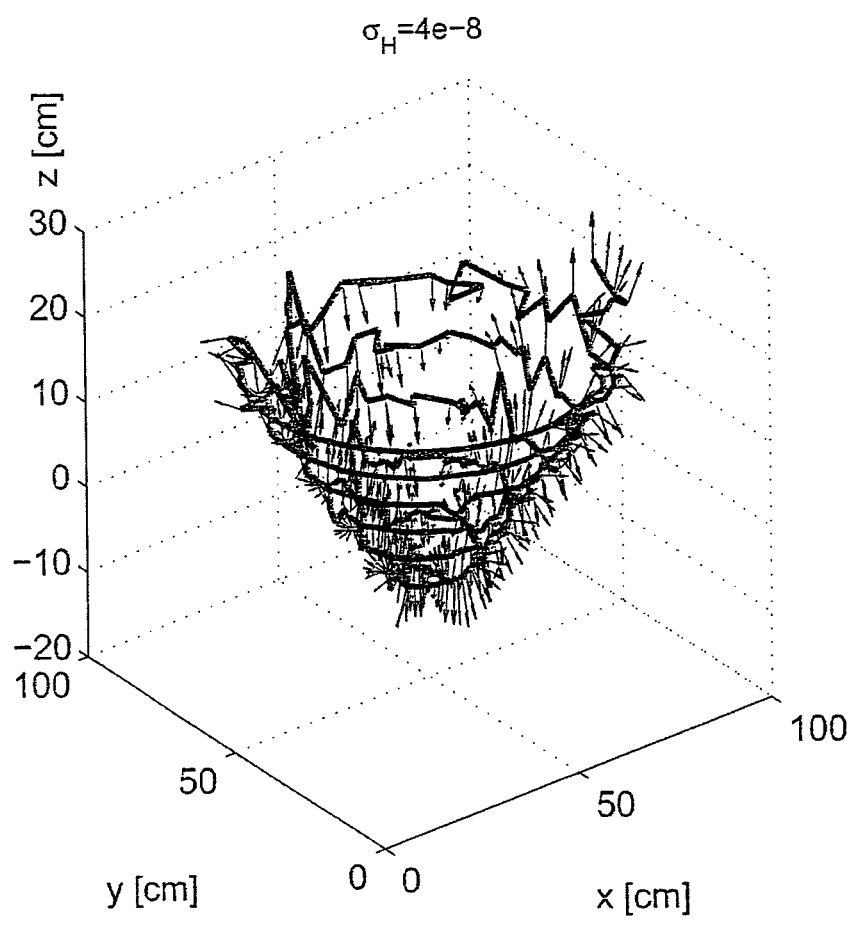
Figure 13:
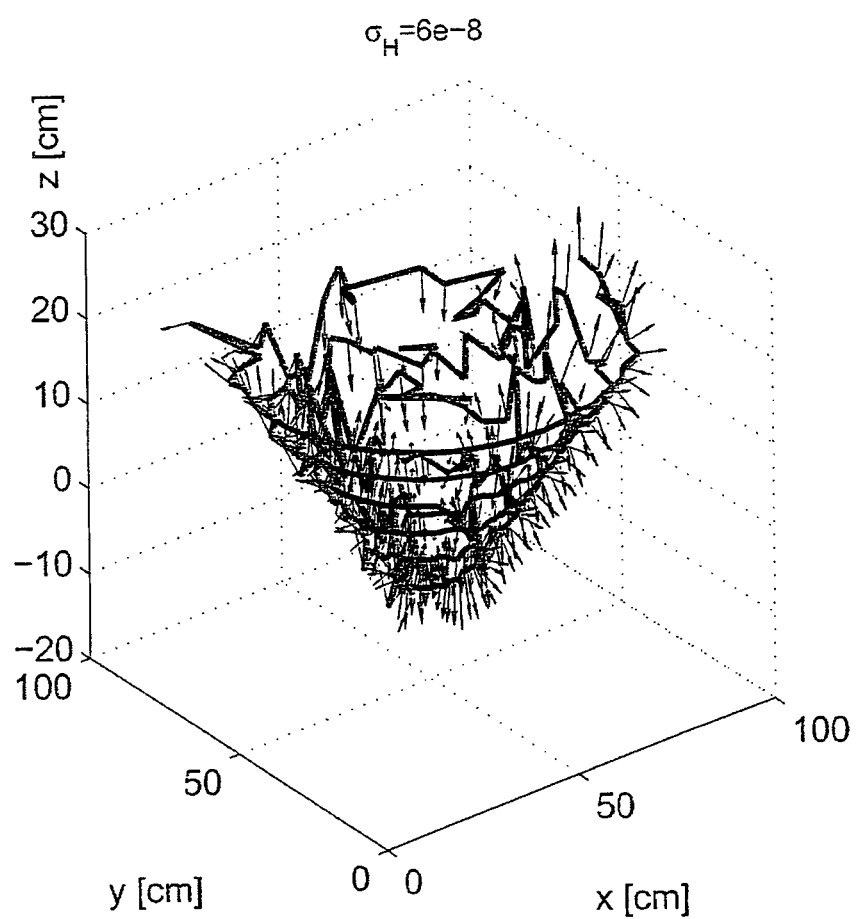
Figure 14:
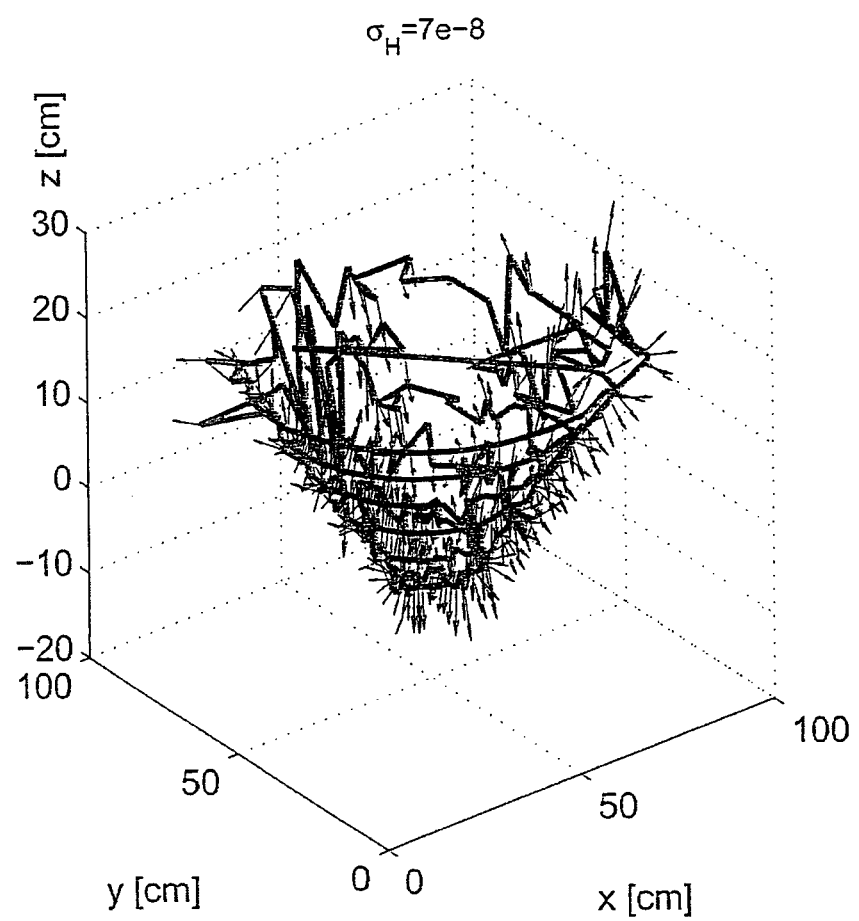

Throughout the present example, the lower frame rate of the Reconstruction from field readings with noise section (supra) was used: a frame every 0.525 cm at the spiral bottom, and every 4.5 cm at the spiral top. FIG. 10 shows the corresponding field readings for the low frame rate when substantially no noise is presented ($\sigma_H = 0$). Subsequently, the noise according to Equation (15) was added, with v increasing from $1 \times 10^{-8}$ to $7 \times 10^{-8}$ in steps of $1 \times 10^{-8}$. The reconstruction quality gradually deteriorated, with FIGS. 11-14 showing typical results. FIG. 11 shows the reconstructed trajectory with $\sigma_H = 1 \times 10^{-8}$; FIG. 12 shows the reconstructed trajectory with $\sigma_H = 4 \times 10^{-8}$; FIG. 13 shows the reconstructed trajectory with $\sigma_H = 6 \times 10^{-8}$; and FIG. 14 shows the reconstructed trajectory with $o = 7 \times 10^{-8}$.

Figure 15:
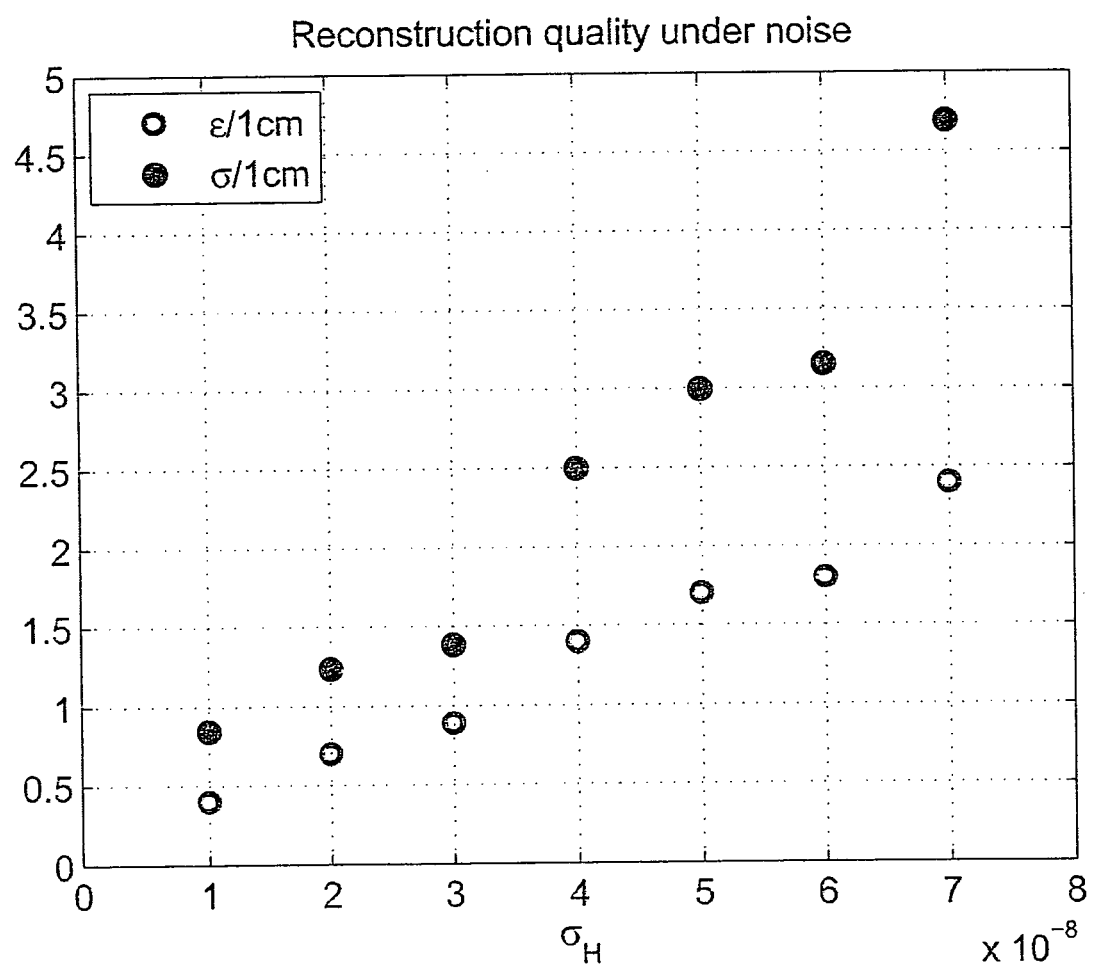
FIG. 15 is a graphic depiction of reconstruction trajectory quality under noisy data according to an embodiment of the present invention.

Finally, the reconstruction quality using the error measures in Equation (14) vs. the noise level was checked quantitatively. The results are shown in FIG. 15, which is a chart of reconstruction quality under noisy data, tested with the global error measures of Equation (14), and for low frame rate. It may be seen that the location error due to these noise levels did not exceed 5 cm.

Robust Solution Procedure for the System of Equations

The solution procedure described above uses an iterative approach that may require a reasonable first guess of the sensor location, for every new point in the sensor trajectory. Hence, for point #1, one may need an external input for this first guess of the sensor location. For point #n; n>1, it may be assumed that the location of point #n-1 is close by and may be known, and this data may be used as a first guess. In some applications this assumption may be too optimistic, and one may need a robust algorithm that treats each point as a new problem and does not assume any prior knowledge about a reasonable first guess.

A robust localization algorithm can be developed directly from equations (3) and (8). At a given point $$f_i = \frac{1}{4\pi r^3}\hat{n}T_d m_i, g_i = \frac{3}{8\pi r^4}\hat{n}T_q Q_i, i = 1, 2, 3. \quad (16)$$

wherein i counts the three possible independent dipole (and quadrupole) excitations. According to some embodiments, an efficient choice for the three dipole excitations may be the column vectors $m_1 = M(1,0,0)'$, $m_2 = M(0,1,0)'$, $m_3 = M(0,0,1)'$. These may be expressed collectively as the excitation matrix MI where I is the 3×3 identity matrix. Similar choice can be done for the three quadrupole excitations (for example, with Q replacing M). The equations in (16) can now be written as, $$f = \frac{M}{4\pi r^3}\hat{n}T_d, \quad (17a)$$

and $$g = \frac{3Q}{8\pi r^4}\hat{n}T_q \quad (17b)$$

where f, g are 3-elements row vectors representing the responses (field readings by the coil sensor) to the three canonical excitations defined above.

It may be verified that $|T_d(\theta,\phi)| = 2 \forall \theta, \phi$. Hence the inverse $T_d^{-1}$ may always exist, and may be computed for every $\theta, \phi$. Applying a right-side multiplication of $T_d^{-1}$ on Eq. (17a) may obtain $$fT_d^{-1} = \frac{M}{4\pi r^3}\hat{n}. \quad (18)$$

wherein $\hat{n}$ is a unit vector (which denotes the coil orientation in space). Therefore the norm of both sides of the equation above may give $M/(4\pi r^3)$. It follows that $$\hat{n} = \frac{fT_d^{-1}}{\|fT_d^{-1}\|}, r = \left[\frac{M}{4\pi\|fT_d^{-1}\|}\right]^{1/3} \quad (19)$$

According to one embodiment, the right hand sides of these expressions may depend only on $\vartheta, \phi$. The expressions for $\hat{n}$ and r above can be substituted into the right hand side of Eq. (17b). The result is $$g = \frac{3}{8}\left(\frac{4}{M}\right)^{4/3} Q\pi^{1/3}\|fT_d^{-1}\|^{1/3} fT_d^{-1}T_q \quad (20)$$

This equation may be a basis of the robust localization algorithm. In some embodiments, g on the left may be a known vector (measurements of the quadrupole fields). Likewise, the quantities Q, M and the vector f on the right side may be known. The matrices $T_d, T_d^{-1}, T_q$ on the right depend only on the angles $\vartheta, \phi$ (the direction to the coil location). Their specific dependencies on these angles may be known [see equations (2a) and (2.7a)]. Hence, the only unknowns in Eq. (20) above are $\vartheta, \phi$; the equation has to be solved for these two unknowns. Therefore, we suggest the following algorithm:

1. define $\tilde{g}(\theta, \phi) = \frac{3}{8}\left(\frac{4}{M}\right)^{4/3} Q\pi^{1/3} \|fT_d^{-1}\|^{1/3} fT_d^{-1} T_q$ 2. scan the two dimensional space $\theta, \phi$ over a rectangular grid with a prescribed resolution $\Delta\theta, \Delta\phi$. Compute the two dimensional array $\tilde{g}(\theta_i, \phi_j)$, with $(\theta_i, \phi_j) = (i\Delta\theta, j\Delta\phi)$
3. by scanning the array, find the value of i, j that minimize the distance $\|g - \tilde{g}(\theta_i, \phi_j)\|/\|g\|$. The corresponding $(\theta_i, \phi_j)$ are the (approximate) solution for the direction angles $\theta, \phi$
4. use the solution for $\theta, \phi$ to find r and $\hat{n}$ via Eq. (19)

Due to the robust scan process of this algorithm, it does not need an initial "reasonable" guess. This may require having to scan a two dimensional space $\theta, \phi$. Such a scan over the domain $0 < \theta < 180°$, $0 < \phi < 180°$ at a resolution of $\Delta\theta = \Delta\phi = 1°$ may be of reasonable complexity to be performed with, for example, a desktop PC.

Figure 16:
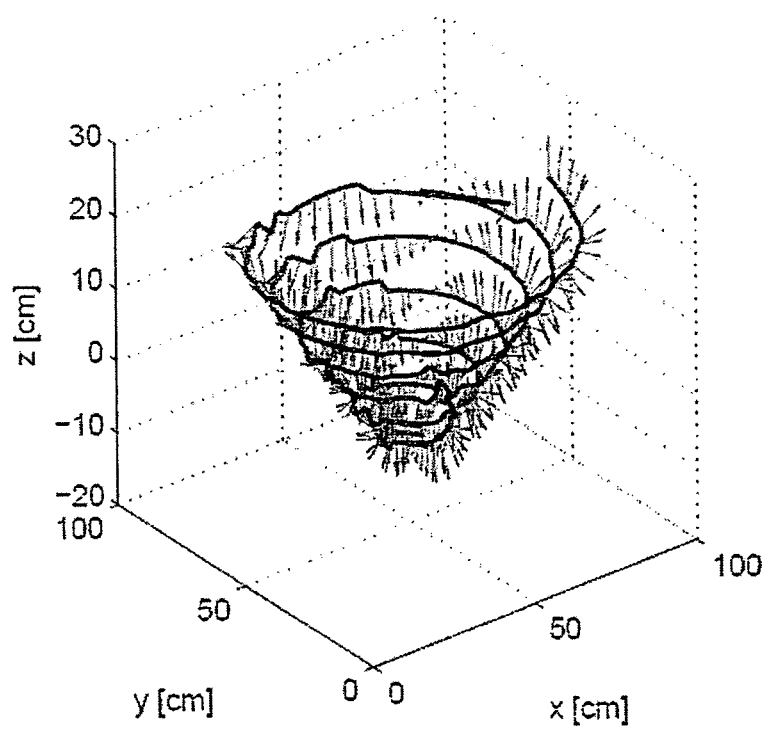
FIG. 16 is a schematic depiction of reconstructed trajectory using the robust algorithm, according to embodiments of the present invention.
Figure 17:
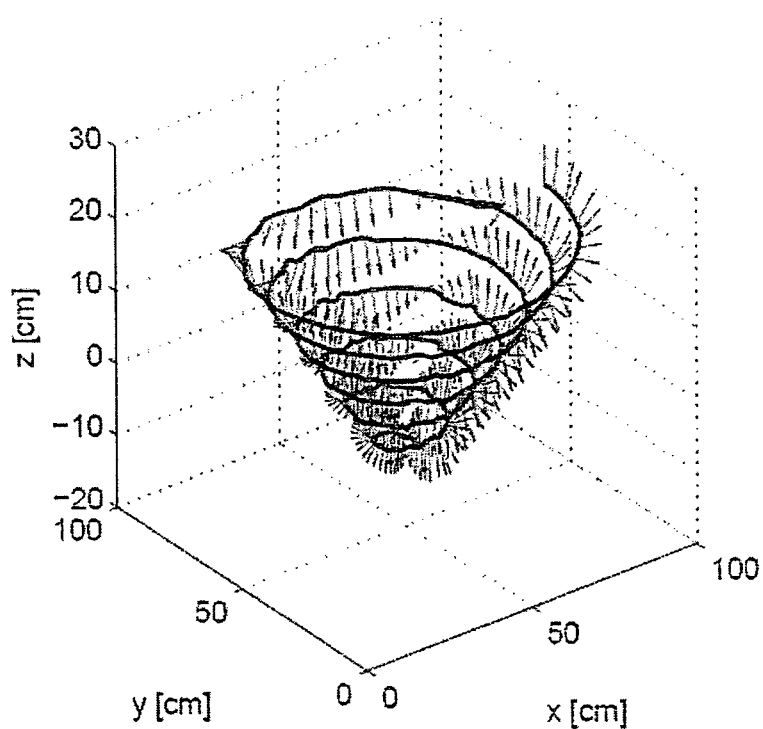
FIG. 17 is a schematic depiction of the reconstructed trajectory of FIG. 16 but with a scan resolution of 0.5°, according to embodiments of the present invention.

As a preliminary demonstration of the above algorithm performance, it may be used to reconstruct the trajectory in FIG. 4, for example at a low frame rate (a frame every 6° on the spiral—details of this synthetic trajectory in are disclosed in Reconstruction from field readings without noise section hereinabove). The $\theta, \phi$ scan was performed at a resolution of $\Delta\theta = \Delta\phi = 1°$. The reconstructed trajectory using the robust algorithm above, with 1° resolution of the $\theta, \phi$ scan is shown in FIG. 16. The reconstruction accuracy is within the range of 5 cm. FIG. 17 shows the same reconstruction, but with a scan resolution of 0.5°, which may provide improved accuracy.

in some embodiments, the reconstruction may be improved by invoking one (or all) of the following approaches:
(i) decrease the scan step
(ii) use the robust algorithm as a mean for obtaining a good first guess, and then invoke the Newton procedure developed hereinabove.

The processes presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems appears from the description herein. In addition, embodiments of the present invention are not described with reference to any particular programming language. It will be appreciated that a variety of programming languages may be used to implement the teachings to of the invention as described herein.

Unless specifically stated otherwise, as apparent from the discussions herein, it is appreciated that throughout the specification discussions utilizing terms such as "estimating," "processing," "computing," "calculating," "determining," or the like, typically refer to the action and/or processes of a computer or computing system, or similar electronic computing device (e.g., a "computer on a chip" or ASIC), that manipulate and/or transform data represented as physical, such as electronic, quantities within the computing system's registers and/or memories into other data similarly represented as physical quantities within the computing system's memories, registers or other such information storage, transmission or display devices.

It will be appreciated by persons skilled in the art that the present invention is not limited to what has been particularly shown and described hereinabove. While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

Having described preferred embodiments of the invention with reference to the accompanying drawings, it is to be understood that the invention is not limited to the precise embodiments shown and described hereinabove. Rather, various changes and modifications may be effected therein by those skilled in the art without departing from the scope or spirit of the invention, and the scope of the present invention is defined only by the claims, which follow.

What is claimed is:

1. A system comprising:
an encapsulated in-vivo imaging device, comprising a single electromagnetic sensor coil for determining localization of said in vivo imaging device in a vicinity of an electromagnetic field, said localization computed based on determining an electrical signal across said electromagnetic sensor coil, said signal being induced by said electromagnetic field;
a set of quadrupole electromagnetic radiator source coils to radiate said electromagnetic field, said electromagnetic field being sensed by said electromagnetic sensor coil, and said set of electromagnetic radiator source coils being located outside of said encapsulated in-vivo imaging device;
wherein said set of quadrupole electromagnetic radiator source coils comprises three mutually orthogonal pairs of parallel coils, and wherein a distance between said parallel coils within said pair is substantially smaller than a distance between said electromagnetic radiator source coils and said electromagnetic sensor coil.

2. The system of claim 1, further comprising an analog-to-digital converter, wherein said converter is used for detecting an electrical signal generated by said radiated electromagnetic field across said electromagnetic sensor coil within said in-vivo imaging device for purposes of localization of said device.

3. The system of claim 1, further comprising a DC-DC converter, wherein said converter is used for delivering power to said in-vivo device.

4. The system of claim 3, wherein said electromagnetic sensor coil is part of said DC-DC converter.

5. The system of claim 1, further comprising a transceiver, wherein said transceiver is to transmit information from and receive information by said in-vivo imaging device.

6. The system of claim 5, wherein said electromagnetic sensor coil is used as an antenna by said transceiver for transmitting information from and receiving information by said in-vivo imaging device.

7. The system of claim 1, wherein said encapsulated in-vivo imaging device further comprising an analog-to-digital converter, a DC-DC converter, a transceiver and means for switching between said coil, and said analog-to-digital converter, said DC-DC converter, and said transceiver within said in-vivo imaging device.

8. The system of claim 1, further comprising a power source to deliver power to said in-vivo device.

9. The system of claim 1, further comprising means for processing information generated in said in-vivo device.

10. The system of claim 1, further comprising a processor and interface circuitry means for controlling said in-vivo device.

11. The system of claim 1, further comprising illumination means for illuminating a body lumen being imaged by said in-vivo device.

12. The system of claim 1, further comprising an imager.

13. The system of claim 1, further comprising a transceiver to transmit data to and receive data from said in-vivo imaging device, said transceiver located outside a body lumen or a cavity being imaged.

14. The system of claim 1, further comprising a magnetic locator located outside a body lumen being imaged.

15. The system of claim 1, further comprising a digital-to-analog converter located outside a body lumen being imaged, said converter used to deliver current to said magnetic source for determining localization of said in vivo imaging device.

16. A method comprising:
 radiating an electromagnetic field by passing a current through a set of quadrupole electromagnetic radiator source coils, said set comprised of three mutually orthogonal pairs of parallel coils;
 sensing said radiated electromagnetic field by a single electromagnetic coil sensor located inside an encapsulated in-vivo imaging device; and
 inferring a location of said in-vivo imaging device with respect to said set of electromagnetic radiator source coils based on an electrical signal excited across said electromagnetic coil sensor by said electromagnetic field.

17. The method of claim 16, comprising using said electromagnetic sensor coil for DC-DC conversion in order to supply power to said in-vivo device.

18. The method of claim 16, further comprising using said electromagnetic sensor coil to transmit information from and receive information by said in-vivo device.

19. The method of claim 16, further comprising operating a switch to use said electromagnetic sensor coil to sense an electromagnetic field irradiated by the coil quadrupole electromagnetic radiator source coils, or as part of a DC-DC voltage converter, or to transmit and receive information.

20. The method of claim 19, wherein operating the switch comprises using a time division multiplexing scheme.

* * * * *